(12) United States Patent
Yamaguchi et al.

(10) Patent No.: US 11,143,643 B2
(45) Date of Patent: Oct. 12, 2021

(54) HUMIDITY MEASUREMENT DEVICE, CONTROL DEVICE FOR INTERNAL COMBUSTION ENGINE, AND ABNORMALITY DETECTION DEVICE

(71) Applicant: DENSO CORPORATION, Kariya (JP)

(72) Inventors: Junzo Yamaguchi, Kariya (JP); Teruaki Kaifu, Kariya (JP)

(73) Assignee: DENSO CORPORATION, Kariya (JP)

( * ) Notice: Subject to any disclaimer, the term of this patent is extended or adjusted under 35 U.S.C. 154(b) by 310 days.

(21) Appl. No.: 16/424,618

(22) Filed: May 29, 2019

(65) Prior Publication Data

US 2019/0277820 A1    Sep. 12, 2019

Related U.S. Application Data

(63) Continuation of application No. PCT/JP2017/044465, filed on Dec. 12, 2017.

(30) Foreign Application Priority Data

Jan. 31, 2017   (JP) .............................. JP2017-015284

(51) Int. Cl.
| | |
|---|---|
| *G01N 33/00* | (2006.01) |
| *G01N 27/00* | (2006.01) |
| *G01N 27/04* | (2006.01) |
| *G01N 27/22* | (2006.01) |
| *G01N 27/12* | (2006.01) |

(Continued)

(52) U.S. Cl.
CPC .............. *G01N 33/007* (2013.01); *F02P 5/04* (2013.01); *G01N 27/00* (2013.01); *G01N 27/04* (2013.01); *G01N 27/12* (2013.01); *G01N 27/22* (2013.01); *G01N 33/0036* (2013.01); *F02D 2200/0418* (2013.01)

(58) Field of Classification Search
CPC ............. G01N 33/0006; G01N 33/007; G01N 27/4175; G01N 27/4163; G01N 33/0004; G01N 27/00; G01N 27/04; G01N 27/22; G01N 27/12; G01N 33/0036; G01M 15/042; G01M 15/10; G01M 15/102; G01M 15/104; G01M 15/106; G01M 15/108; F02P 5/04; F02D 2200/0418; F02D 2041/285; F02D 41/222; F02D 41/18; Y02T 10/40

See application file for complete search history.

(56) References Cited

U.S. PATENT DOCUMENTS

| | | | |
|---|---|---|---|
| 2013/0269419 A1 | 10/2013 | Etherington et al. | |
| 2017/0016415 A1* | 1/2017 | Hoshika | ........... F02M 35/10393 |

FOREIGN PATENT DOCUMENTS

| | | |
|---|---|---|
| JP | 5-157714 | 6/1993 |
| JP | 6-288950 | 10/1994 |

(Continued)

*Primary Examiner* — Peter J Macchiarolo
*Assistant Examiner* — Anthony W Megna Fuentes

(57) ABSTRACT

A humidity measurement device is configured to measure a humidity of a gas. The humidity measurement device includes: a second-order calculation part to calculate a second-order differential value by performing second-order differentiation by time on a humidity signal output from a humidity detection part; and an adherence determination part to determine whether a liquid has adhered to the humidity detection part based on the second-order differential value obtained by the second-order calculation part.

11 Claims, 12 Drawing Sheets

(51) Int. Cl.
    *F02P 5/04*          (2006.01)
    *F02D 41/28*       (2006.01)
    *F02D 41/22*       (2006.01)
    *F02D 41/18*       (2006.01)

(56) References Cited

FOREIGN PATENT DOCUMENTS

| | | |
|---|---|---|
| JP | 2003-185614 | 7/2003 |
| JP | 2011-52564 | 3/2011 |
| JP | 2013-234598 | 11/2013 |
| JP | 2014-196703 | 10/2014 |
| WO | 2018/100887 | 6/2018 |
| WO | 2018/147004 | 8/2018 |

\* cited by examiner

HUMIDITY MEASUREMENT DEVICE, CONTROL DEVICE FOR INTERNAL COMBUSTION ENGINE, AND ABNORMALITY DETECTION DEVICE

CROSS REFERENCE TO RELATED APPLICATION

The present application is a continuation application of International Patent Application No. PCT/JP2017/044465 filed on Dec. 12, 2017, which designated the U.S. and claims the benefit of priority from Japanese Patent Application No. 2017-15284 filed on Jan. 31, 2017. The entire disclosures of all of the above applications are incorporated herein by reference.

TECHNICAL FIELD

The present disclosure relates to a humidity measurement device, a control device for an internal combustion engine, and an abnormality detection device.

BACKGROUND

Conventionally, a humidity measurement device has been provided for measuring a humidity of an intake air taken into an internal combustion engine. The humidity measurement device has a sensor element for detecting the humidity. During use of the device, waterdrops may adhere to a surface of the sensor element.

SUMMARY

According to one aspect of the present disclosure, a humidity measurement device, which is to measure a humidity of a gas, is configured to determine whether a liquid has adhered thereto.

BRIEF DESCRIPTION OF THE DRAWINGS

The above and other objects, features and advantages of the present disclosure will become more apparent from the following detailed description made with reference to the accompanying drawings. In the drawings.

DETAILED DESCRIPTION

Figure 1:
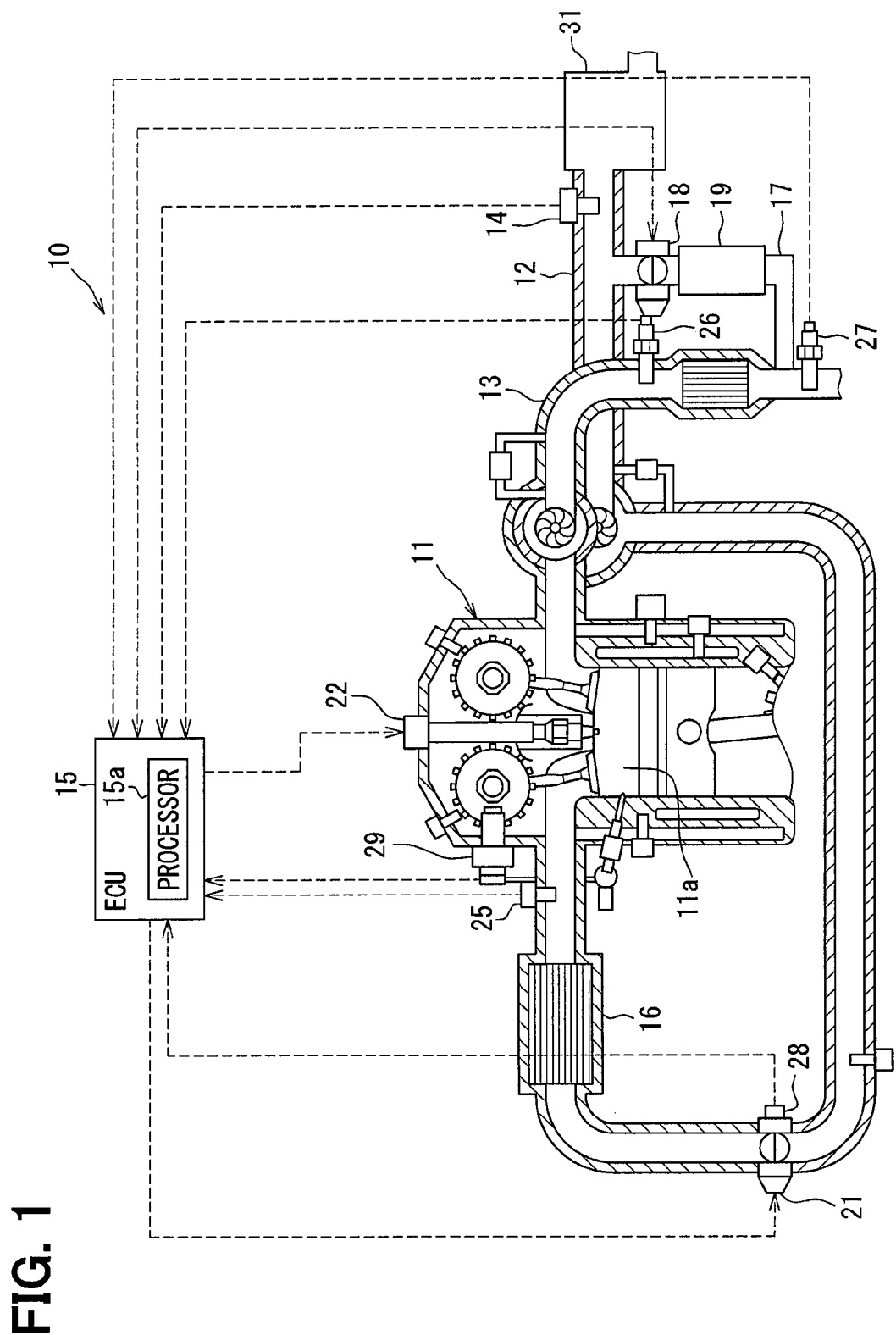
FIG. 1 is a schematic diagram illustrating a configuration of a control system according to a first embodiment.

Hereinafter, an example of the present disclosure will be described.

According to one example, a measurement device is provided to measure a flow amount of an intake air taken into an internal combustion engine. The measurement device includes a temperature sensor to measure a temperature of the intake air and a humidity sensor to measure a humidity of the intake air.

The measurement device is further configured to determine whether or not waterdrops adhere to a surface of a sensor element which is for detecting the humidity.

In an assumable configuration, when the waterdrops adhere to a surface of a humidity sensor, a detection value of the humidity sensor could indicate a humidity of about 100%, and the detection value is clamped at the constant value.

In consideration of that, the assumable configuration calculates an index obtained by dividing a rate of change in the temperature by a rate of change in the humidity by using the temperature and the humidity detected by the temperature sensor and the humidity sensor, respectively, thereby to cause change in the index in response to change in the temperature even in the state where the detection value of the humidity is clamped at the constant value.

The measurement device determines whether or not to continue a state in which the index is larger than a threshold value for a determination time or longer. Subsequently, the measurement device recognizes that the waterdrop has adhered to the surface of the humidity sensor when the state continues for the determination time or longer.

It is noted that, water drops may also adhere to the temperature sensor. In this case, it is conceivable that the detection value of the temperature sensor does not change from a predetermined value. Conceivably, in a case where waterdrops adhere to both of the temperature sensor and the humidity sensor, the index may not exhibit an appropriate value. Consequently, an issue arises that the waterdrops adhered to the humidity sensor cannot be determined with high precision according to the index.

It is further noted that, the assumable configuration determines whether or not the state, in which the index is larger than the threshold value, continues for the determination time or longer. Therefore, the assumable configuration requires at least the determination time from a time point when the adherence of the waterdrop to the humidity sensor actually occurs to a time point when the adherence of the waterdrop to the humidity sensor can be detected. For that reason, the assumable configuration requires at least the determination time to make the determination even when no waterdrop has adhered to the surface of the humidity sensor. Thus, the assumable configuration could exhibit low responsiveness in determination whether the adherence of the waterdrop has occurred According to a first aspect of the present disclosure, a humidity measurement device is configured to measure a humidity of a gas. The humidity measurement device comprises a second-order calculation part configured to calculate a second-order differential value by performing second-order differentiation by time on a humidity signal output from a humidity detection part. The humidity measurement device further comprises an adherence determination part configured to determine whether a liquid has adhered to the humidity detection part based on the second-order differential value obtained by the second-order calculation part.

According to a second aspect of the present disclosure, a control device is for an internal combustion engine, the control device configured to control an operation state of an internal combustion engine supplied with an intake air. The control device comprises a humidity obtaining part configured to obtain a humidity of the intake air based on a humidity signal output from a humidity detection part according to the humidity of the intake air. The control device further comprises a parameter setting part configured to set an obtaining result of the humidity obtaining part as one of parameters for controlling the operation state of the internal combustion engine. The control device further comprises a second-order calculation part configured to calculate a second-order differential value by performing a second-order differentiation by a time on the humidity signal. The control device further comprises an adherence determination part configured to determine whether a liquid has adhered to the humidity detection part based on the second-order differential value obtained from the second-order calculation part. The control device further comprises a substitute setting part configured to set a predetermined substitute humidity for the humidity of the intake air as one of parameters, instead of the obtaining result by the humidity detection part, in response to determination of the adherence determination part that a liquid has adhered to the humidity detection part.

According to a third aspect of the present disclosure, an abnormality detection device is configured to detect an adherence of a liquid to a humidity detection part, which is configured to output a humidity signal according to a humidity of a gas as an abnormality. The abnormality detection device comprises a second-order calculation part configured to calculate a second-order differential value by performing a second-order differentiation by a time on the humidity signal. The abnormality detection device further comprises an adherence determination part configured to determine whether the liquid has adhered to the humidity detection part based on the second-order differential value obtained from the second-order calculation part.

The present inventors have obtained such a knowledge that when the adherence of the liquid to the humidity detection part occurs and when the adhered liquid is dried and eliminated, a change mode of the humidity signal output from the humidity detection part is steeper than that when the humidity actually changes. According to the above knowledge, the steepness of an increase or a decrease of the humidity signal is determined based on a second-order differential value which is a rate of change in the rate of change of the humidity signal, thereby being capable of discriminating between a case in which the adherence of the liquid occurs and a case in which the humidity actually changes without the adherence of the liquid. Further, according to the above knowledge, the case in which the liquid adhered to the humidity detection part is lost and the case where the liquid is not lost can be discriminated.

According to each of the above aspects, the device uses the second-order differential value of the humidity signal to determine whether or not the liquid has adhered to the humidity detection part. Therefore, the device does not require to use, for example, the temperature detected by the temperature detection part in determination of adherence of waterdrops.

The device determines, for example, whether or not the increase in the humidity is steep by using the second-order differential value, thereby to enable to distinguish the occurrence of the adherence of the liquid to the humidity detection part from the actual increase in the humidity. In addition, the device makes determination on whether or not the decrease in the humidity is steep by using the second-order differential value, thereby to enable to determine whether or not the liquid adhered to the humidity detection part is lost with high precision. In addition, the device does not require to wait for the predetermined period of time to confirm that the detection value of the humidity detection part does not change from the predetermined value. Therefore, the device enables to enhance the responsiveness of the determination while enhancing the determination accuracy with respect to the fact that the liquid has adhered to the humidity detection part. In other words, the device enables to properly grasp the adherence of the liquid to the humidity detection part.

Hereinafter, a plurality of embodiments of the present disclosure will be described with reference to the drawings. Incidentally, the same reference numerals are assigned to the corresponding components in each embodiment, and thus, duplicate descriptions may be omitted. When only a part of the configuration is described in each embodiment, the configuration of the other embodiments described above can be applied to the other parts of the configuration. Further, not only the combinations of the configurations explicitly shown in the description of the respective embodiments, but also the configurations of the plurality of embodiments can be partially combined even if the combinations are not explicitly shown if there is no problem in the combination in particular. Unspecified combinations of the configurations described in the plurality of embodiments and the modification examples are also disclosed in the following description.

First Embodiment

A control system 10 shown in FIG. 1 includes an internal combustion engine 11 such as a diesel engine, an intake flow channel 12, an exhaust flow channel 13, an air flow meter 14, and an ECU (Engine Control part) 15. The control system 10 includes an EGR (Exhaust Gas Recirculation) system capable of adjusting an EGR amount. The EGR system includes an intercooler 16, an EGR flow channel 17, an EGR valve 18, and an EGR cooler 19. The internal combustion engine 11 may be a gasoline engine or the like in addition to a diesel engine.

The air flow meter 14 is provided in the intake flow channel 12, and has a function of measuring a physical quantity such as a flow rate, a temperature, a humidity, and a pressure with respect to an intake air supplied to the internal combustion engine 11. The intake air is a gas supplied to a combustion chamber 11a of the internal combustion engine 11.

The ECU 15 is a calculation processing circuit configured by a processor 15a, a storage medium such as a RAM, a ROM, and a flash memory, a microcomputer including an input and output part, a power supply circuit, and the like. A sensor signal output from the air flow meter 14, a sensor signal output from a large number of vehicle-mounted sensors, and the like are input to the ECU 15. The ECU 15 performs an engine control for an opening degree of a throttle valve 21, a fuel injection amount of an injector 22, and an opening degree of an EGR valve 18 with the use of a measurement result by the air flow meter 14. The ECU 15 corresponds to a control device for the internal combustion engine for controlling the operation of the internal combustion engine 11, and the control system 10 may be referred to as an engine control system.

The air flow meter 14 is one of a number of measuring parts included in the control system 10. In an intake system and an exhaust system of the internal combustion engine 11, for example, an intake air temperature sensor 25, an air-fuel ratio sensor 26, an oxygen sensor 27, a throttle opening sensor 28, and the like are provided in addition to the air flow meter 14 as measuring parts. The internal combustion engine 11 is provided with a crank angle sensor 29 and the like as a measuring part.

In the intake flow channel 12, the air flow meter 14 is located on a downstream side of an air cleaner 31. The air flow meter 14 is located on an upstream side of a connection part between the intake flow channel 12 and the EGR flow channel 17. In the above configuration, the air flow meter 14 is less likely to be exposed to a gas flowing out of the EGR flow channel 17.

The air flow meter 14 measures not only an intake air flow rate but also a humidity of the intake air with high response and high accuracy, thereby being capable of performing an optimum control of the EGR amount, and contributing to a low fuel consumption and a low exhaust gas of the internal combustion engine 11. The air flow meter 14 outputs flow rate information corresponding to the flow rate of the intake air flowing through the intake flow channel 12 of the internal combustion engine 11 and temperature information and humidity information corresponding to the temperature and humidity of the intake air flowing through the intake flow channel 12 to the ECU 15 which is an external device. In the following description, an inlet side of the intake flow channel 12 into which an air is introduced is defined as the upstream side of the intake flow channel 12, and the combustion chamber 11a side is defined as the downstream side of the intake flow channel 12.

Figure 2:
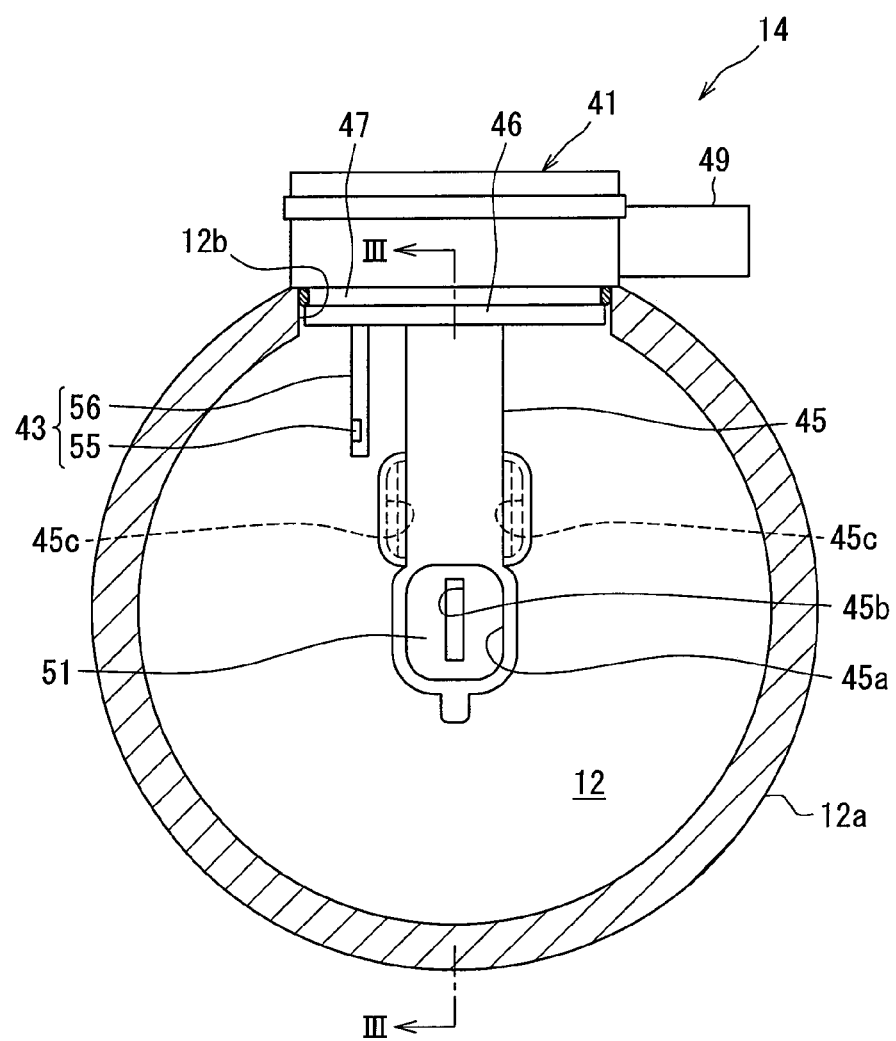
FIG. 2 is a front view of an air flow meter in a state in which the air flow meter is adhered to an intake pipe.
Figure 3:
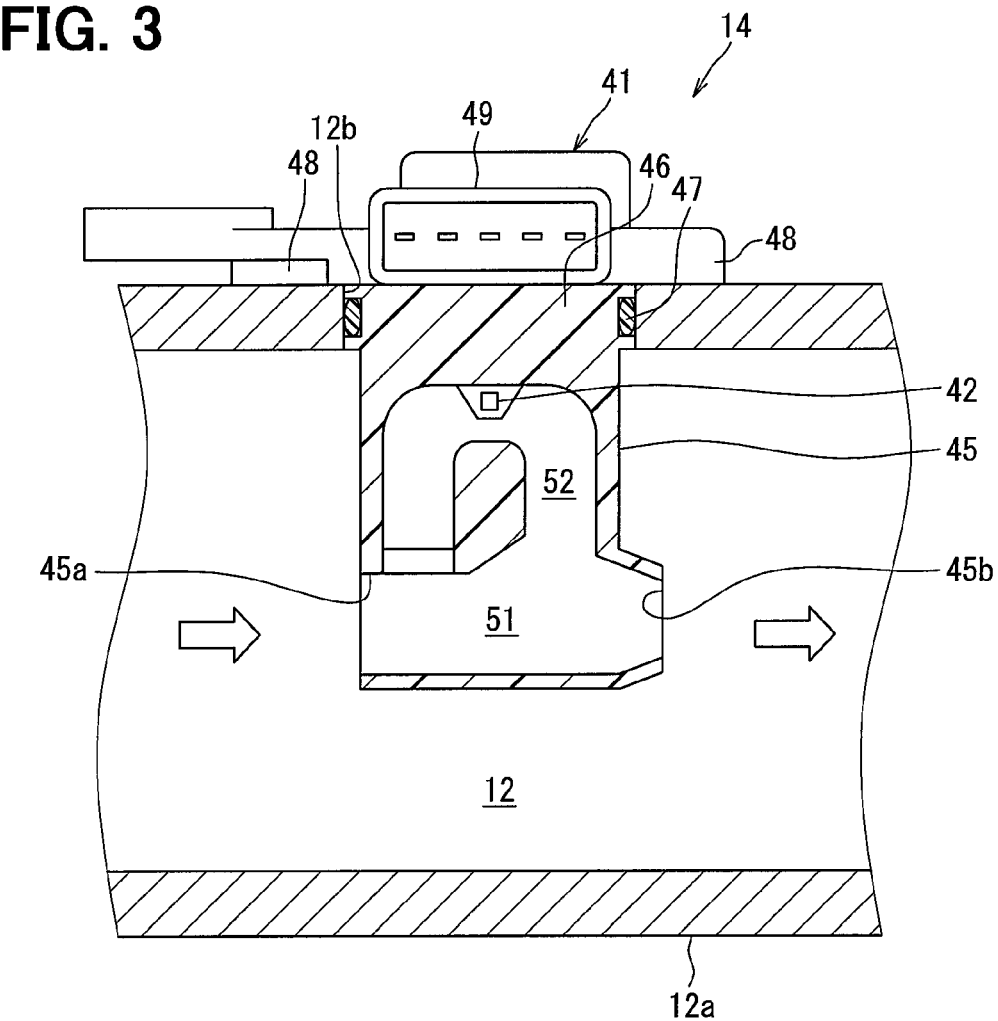
FIG. 3 is a cross-sectional view taken along a line III-III of FIG. 2.

The air flow meter 14 shown in FIGS. 2 and 3 is detachably adhered to an intake pipe 12a providing the intake flow channel 12. The air flow meter 14 is inserted into a sensor insertion hole 12b provided to penetrate through a cylindrical wall of the intake pipe 12a, and at least a part of the air flow meter 14 is positioned in the intake flow channel 12. The air flow meter 14 includes a housing 41, a flow rate detection part 42, a sensor unit 43, and a signal processing part 44 (refer to FIG. 6).

The housing 41 is made of, for example, a resin material or the like. In the air flow meter 14, since the housing 41 is adhered to the intake pipe 12a, the flow rate detection part 42 and the sensor unit 43 are brought into contact with the intake air flowing through the intake flow channel 12. The housing 41 is provided with a bypass part 45, a fitting part 46, an O-ring 47, a fixing part 48, a connector part 49, and the like.

The bypass part 45 provides bypass passages 51 and 52. The bypass passages 51 and 52 introduce a part of the intake air flowing through the intake flow channel 12 into the interior of the housing 41. The main bypass passage 51 penetrates through the bypass part 45, and an upstream side end portion of the main bypass passage 51 provides an inflow port 45a and a downstream side end portion of the main bypass passage 51 provides a main outflow port 45b. The sub-bypass passage 52 branches from an intermediate portion of the main bypass passage 51, and is shaped to surround the inside of the bypass part 45. The downstream side end portion of the sub-bypass passage 52 provides a sub-outflow port 45c. FIG. 2 is a view of the air flow meter 14 as seen from the side of the inflow port 45a.

The fitting part 46 is a portion that is fitted into the sensor insertion hole 12b through the O-ring 47. The O-ring 47 is a member for sealing the intake flow channel 12 and the outside of the intake pipe 12a. The O-ring 47 is externally fitted to the fitting part 46, and is interposed between the fitting part 46 and the sensor insertion hole 12b. The fixing part 48 is a portion for fixing the air flow meter 14 to the intake pipe 12a in a state where a main portion of the housing 41 enters the intake flow channel 12.

The connector part 49 is a portion that surrounds multiple terminals. A plug part is inserted into the connector part 49. The plug part is provided at an end portion of a connecting line electrically connected directly or indirectly to the ECU 15, and the plug part mates with the connector part 49.

The flow rate detection part 42 is, for example, a thermal type flow rate sensor formed of a heat generation resistor. The flow rate detection part 42 is located in the sub-bypass passage 52. When the housing 41 is adhered to the intake pipe 12a, the intake air flowing through the bypass passage 51 is supplied to the flow rate detection part 42. The flow rate detection part 42 is electrically connected to multiple terminals provided in the connector part 49. The flow rate detection part 42 outputs a sensor signal corresponding to the intake air flow rate and corresponding to the flow rate of air flowing through the bypass passage 51 to the signal processing part 44 as a flow rate signal. The flow rate detection part 42 is not limited to the thermal type flow rate sensor, and may be an ultrasound type flow rate sensor or the like.

The sensor unit 43 is located on a side of the bypass part 45 of the housing 41. The sensor unit 43 includes a sensor chip 55 and a chip support 56. The sensor chip 55 is capable of detecting a temperature and a humidity, and the chip support 56 supports the sensor chip 55 in a state independent of the bypass part 45. The chip support 56 extends from the fitting part 46 and is supported by the housing 41. The sensor chip 55 is located in the intake flow channel 12 by attaching the housing 41 to the intake pipe 12a. The chip support 56 may be provided integrally with the bypass part 45.

The sensor unit 43 is electrically connected to the multiple terminals provided in the connector part 49. The sensor unit 43 outputs a sensor signal corresponding to the humidity of the intake air flowing through the intake flow channel 12 as a humidity signal. The humidity signal is a digital signal. The humidity signal may be an analog signal such as a simple potential. In addition to the humidity signal, the sensor unit 43 outputs a temperature signal corresponding to a temperature of the intake air.

Figure 4:
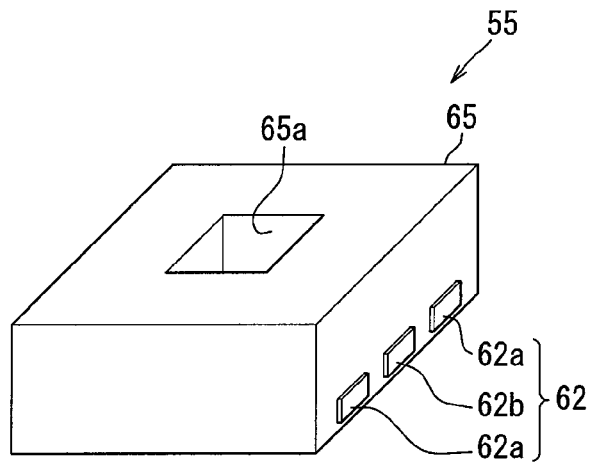
FIG. 4 is a perspective view of a sensor chip.
Figure 5:
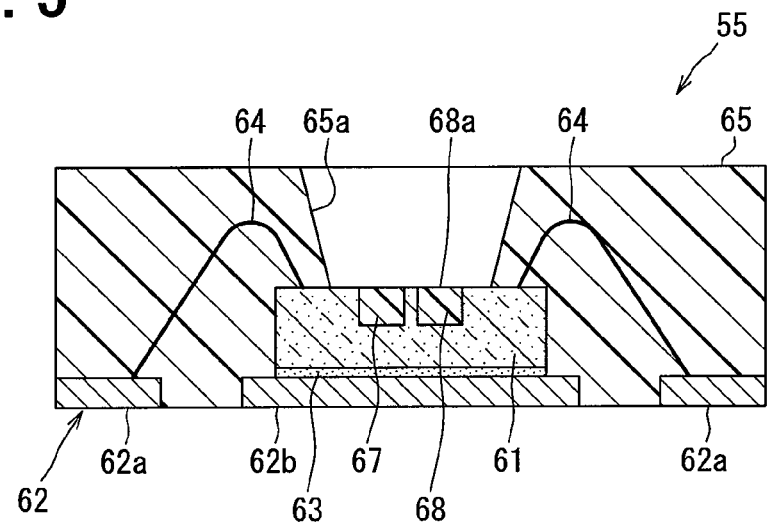
FIG. 5 is a vertical cross-sectional view of the sensor chip.

In the sensor unit 43, the sensor chip 55 is mounted on a sensor substrate, and the sensor substrate is embedded in the chip support 56. The sensor chip 55 shown in FIGS. 4 and 5 is formed as a flat square prism as a whole. The sensor chip 55 includes a chip substrate 61, an electrode plate 62, a bonding material 63, a bonding wire 64, and a sealing part 65.

The chip substrate 61 is made of an insulating material such as silicon, and is formed in a rectangular prism shape which is flat as a whole. A temperature detection part 67 and a humidity detection part 68 are formed on a top face of the chip substrate 61, and those detection parts 67 and 68 are located side by side. The temperature detection part 67 is a temperature sensor for detecting the temperature of a gas such as the intake air. The humidity detection part 68 is a humidity sensor that measures a relative humidity of a gas such as the intake air. The temperature detection part 67 and the humidity detection part 68 output a temperature signal and a humidity signal corresponding to the temperature and humidity of the intake air to the signal processing part 44. The temperature detection part 67 may be directly covered with the sealing part 65 or may be exposed to air.

The humidity detection part 68 is, for example, a capacitive type humidity sensor that measures a capacitance of a moisture sensitive material that absorbs and dehumidifies a moisture contained in the air by a pair of electrodes that sandwich the moisture sensitive material. As the humidity detection part 68, a resistance type humidity sensor, a thermal type humidity sensor, or the like can be employed. The humidity detection part 68 has a detection surface 68a that comes into contact with the intake air as a detection target, and is located in an orientation in which the detection surface 68a is exposed from the chip substrate 61.

The electrode plate 62 is a thin plate-shape member made of a conductive material. The electrode plate 62 forms a bottom surface of the sensor chip 55. A chip electrode 62a, a die pad 62b, and the like are formed on the electrode plate 62. The chip electrode 62a is electrically connected to a wiring provided on the sensor circuit board in a state where the sensor chip 55 is mounted on the sensor substrate.

The bonding material 63 bonds the bottom surface of the chip substrate 61 to the die pad 62b of the electrode plate 62. The bonding wire 64 is a wire-like member made of a conductive material. The bonding wire 64 electrically connect the respective electrodes of the humidity detection part 68 provided on the chip substrate 61 to the chip electrode 62a.

The sealing part 65 is in close contact with the electrode plate 62, and covers the chip substrate 61, the bonding wire 64, and the like. A detection hole 65a is provided in the sealing part 65. The detection hole 65a is a partially conical through hole provided at a position overlapping with the detection parts 67 and 68 formed on the top face of the chip substrate 61. The detection hole 65a exposes the detection parts 67 and 68 from the sealing part 65. In the humidity detection part 68, the detection surface 68a is exposed from the sealing part 65 through the detection hole 65a.

The chip support 56 is made of a resin material in a rectangular thick plate-shape. The chip support 56 covers the sensor chip 55 and the sensor substrate. The chip support 56 exposes the detection parts 67 and 68 to the outside of the chip support 56. A support hole for exposing the detection parts 67 and 68 is provided in the chip support 56, and the support hole is formed at a position overlapping with the detection hole 65a of the sensor chip 55. With the configuration described above, the detection parts 67 and 68 can come in contact the intake air flowing through the intake flow channel 12 (refer to FIG. 1) through the detection hole 65a and the support hole.

Figure 6:
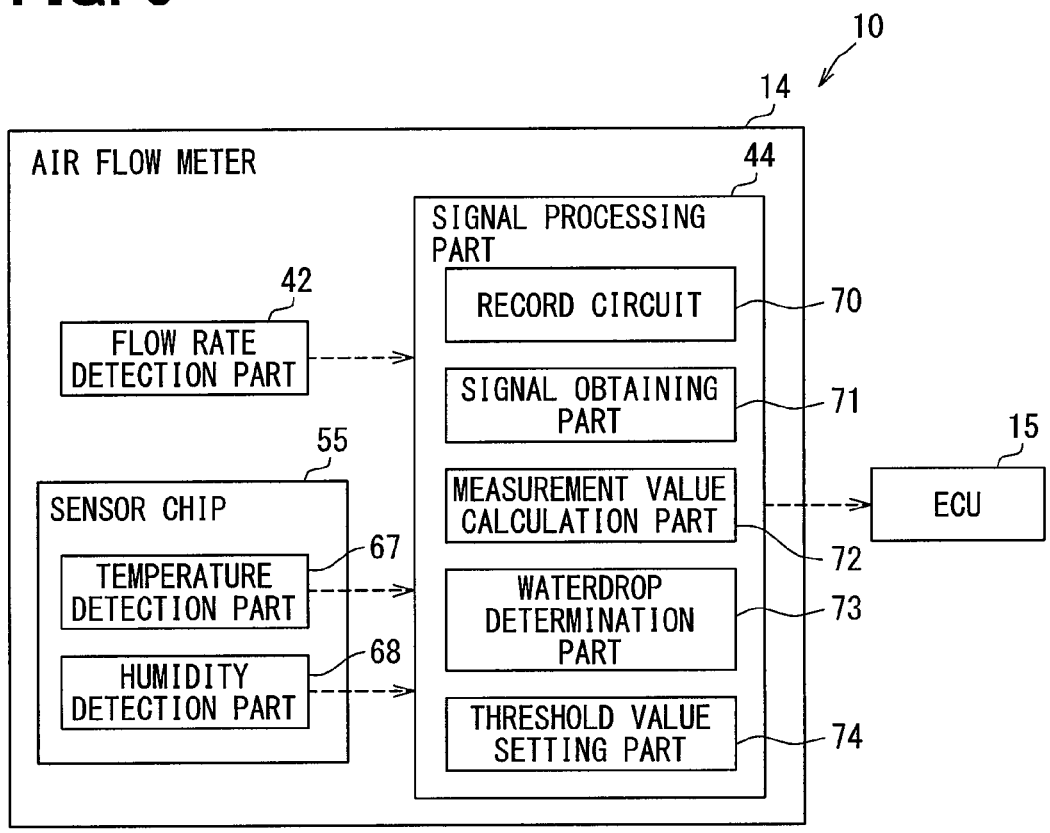
FIG. 6 is a block diagram showing an electrical configuration of the control system.

The signal processing part 44 shown in FIG. 6 is an electronic circuit included in the air flow meter 14 together with the sensor chip 55, and is mounted on the housing 41. The flow rate detection part 42, the temperature detection part 67, and the humidity detection part 68 are electrically connected to the signal processing part 44, and a flow rate signal, a temperature signal, and a humidity signal are input from the detection parts 42, 67, and 68. The signal processing part 44 may be mounted on the sensor chip 55.

The signal processing part 44 includes a storage circuit 70. The storage circuit 70 stores a humidity measurement program and an abnormality detection program which cause the signal processing part 44 to function as a humidity measurement device that measures the humidity of the intake air. According to the execution of the humidity measurement program and the abnormality detection program by the electronic circuit, the signal processing part 44 includes functional blocks such as a signal obtaining part 71, a measurement value calculation part 72, a waterdrop determination part 73, and a threshold value setting part 74. When the ECU 15 is referred to as a first control device, the signal processing part 44 may be referred to as a second control device.

As with the ECU 15, the signal processing part 44 may be a calculation processing circuit including a processor, a storage medium such as a RAM, a ROM and a flash memory, a microcomputer including an input and output part, a power supply circuit, and the like. In the above configuration, the storage medium is a non-transitory tangible storage medium and is not limited to the ROM and storage medium described above. In the above configuration, the signal processing part 44 can also be referred to as an SCU (Sensor Control part).

The signal obtaining part 71 obtains a flow rate signal, a temperature signal, a humidity signal, and the like from the flow rate detection part 42, the temperature detection part 67, the humidity detection part 68, and the like. The measurement value calculation part 72 calculates the measurement result of physical quantities such as the flow rate, the temperature, and the humidity of the intake air based on the flow rate signal, the temperature signal, the humidity signal, and the like obtained by the signal obtaining part 71. The temperature and humidity measured by the measurement value calculation part 72 are stored in the storage circuit 70.

The waterdrop determination part 73 detects that a waterdrop has adhered to the humidity detection part 68 based on the humidity signal output from the humidity detection part 68. Here, it is assumed that a liquid such as condensation water generated in the intake flow channel 12, a water flowing through the intake flow channel 12, or a water flying with the intake air has adhered to the humidity detection part 68 as waterdrops. When the waterdrop has adhered to the humidity detection part 68, a content of the humidity signal output from the humidity detection part 68 may differ from a content indicating the actual humidity of the intake air due to the influence of the waterdrop. That is, there is a possibility that the measurement accuracy of the humidity by the air flow meter 14 is lowered.

In the present embodiment, it is assumed that a waterdrop has adhered to the humidity detection part 68 if the waterdrop has adhered to the detection surface 68a even slightly, and that the waterdrop is not adhered to the humidity detection part 68 if no waterdrop has adhered to the detection surface 68a.

Depending on the detection accuracy of the humidity detection part 68 or the like, it may be assumed that the waterdrop has adhered to the humidity detection part 68 when the waterdrop has adhered to the entire detection surface 68a, and that the waterdrop is not adhered to the humidity detection part 68 when there is a portion in which the waterdrop is not adhered to the detection surface 68a even a little. Further, regarding the detection surface 68a, it may be assumed that the waterdrop has adhered to the humidity detection part 68 when an area to which the waterdrop has adhered is larger than a predetermined value, and that the waterdrop is not adhered to the humidity detection part 68 when the area to which the waterdrop has adhered is not larger than the predetermined value.

The waterdrop determination part 73 calculates a first-order differential value RH1 by performing a first-order differentiation by a time on a humidity RH of the intake air calculated by the measurement value calculation part 72, and calculates a second-order differential value RH2 by performing a second-order differentiation by a time on the humidity RH. The first-order differential value RH1 is dRH/dt, and the second-order differential value RH2 is $d^2RH/dt^2$. The waterdrop determination part 73 compares the second-order differential value RH2 with predetermined threshold values Q1, Q2, and Q3, and further evaluates threshold times Tr1 and Tr2 in the comparison result to determine whether or not the waterdrop has adhered to the humidity detection part 68.

Sensor signals are inputted to the ECU 15 from a vehicle speed sensor, an outside air temperature sensor, an atmospheric pressure sensor, or the like. The ECU 15 obtains at least environmental information such as an outside air temperature and an atmospheric pressure and vehicle information such as a vehicle speed and a cumulative travel distance based on various sensor signals, and outputs those pieces of information to the signal processing part 44.

The threshold value setting part 74 sets the threshold values Q1, Q2, and Q3. The first threshold value Q1 is a threshold value which is set to a positive value for determining whether or not the adherence of the waterdrop to the humidity detection part 68 has occurred. The second threshold value Q2 is a threshold value which is set to a negative value for determining whether or not the waterdrop adhered to the humidity detection part 68 has been eliminated. The third threshold value Q3 is a threshold value used for enhancing the determination accuracy when determining whether or not the adherence of the waterdrop has occurred and for enhancing the determination accuracy when determining whether or not the waterdrop has been eliminated. The threshold value setting part 74 also sets the threshold times Tr1 and Tr2 in addition to the threshold values Q1 to Q3. The threshold values Q1 to Q3 and the threshold time Tr1, Tr2 are set based on, for example, an output specification of the humidity detection part 68, specifically, a variation in the responsiveness of the output, and the like. The first threshold value Q1 corresponds to an occurrence threshold value, the second threshold value Q2 corresponds to a dry threshold value, and the third threshold value Q3 corresponds to an occurrence inflection value and a dry inflection value. The first threshold time Tr1 corresponds to an occurrence threshold time, and the second threshold time Tr2 corresponds to a dry threshold time.

The signal processing part 44 outputs information including the calculation result of the measurement value calculation part 72, the determination result of the waterdrop determination part 73, and the like to the ECU 15. The calculation result of the measurement value calculation part 72 includes the humidity RH, and the determination result of the waterdrop determination part 73 includes water adherence information indicating whether or not the waterdrop has adhered to the humidity detection part 68.

Here, assuming that the vehicle is traveling, an adherence occurrence profile ha indicating a variation mode of the humidity when the adherence of the waterdrop to the humidity detection part 68 has occurred, and a non-adherence profile hb indicating a variation mode of the humidity when the waterdrop is not adhered will be described with reference to FIGS. 7 and 8. For the adherence occurrence profile ha, the respective change modes of the first-order differential value RH1a and the second-order differential value RH2a are illustrated, but for the non-adherence profile hb, the first-order differential value and the second-order differential value are not illustrated.

Figure 7:
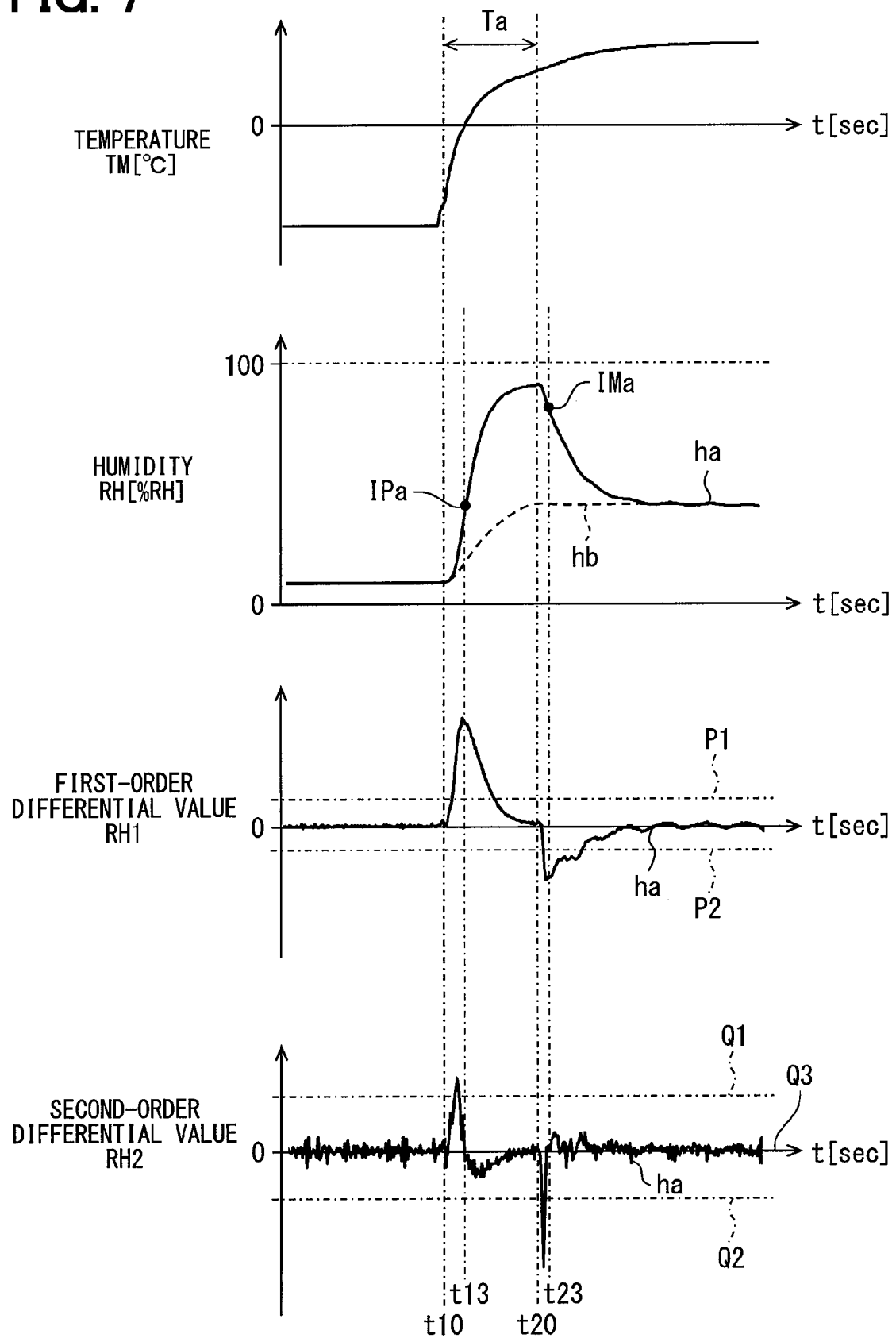
FIG. 7 is a timing chart showing change modes of a humidity, a first-order differential value, and a second-order differential value when waterdrops adhere to a humidity detection part.
Figure 8:
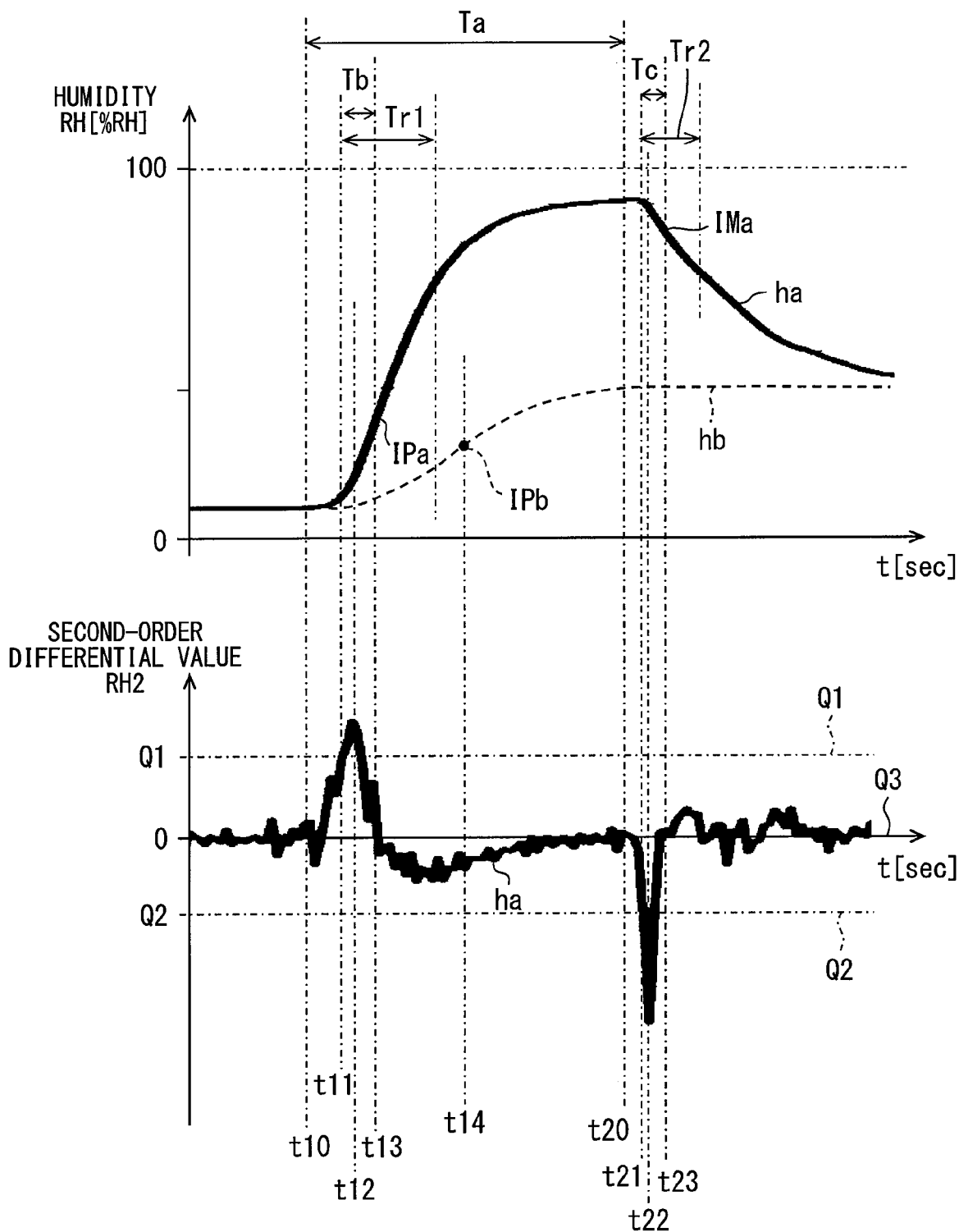
FIG. 8 is a timing chart showing change modes of the humidity and a second-order differential value when waterdrops adhere to the humidity detection part.

FIGS. 7 and 8 exemplify a change mode in the humidity RH of the adherence occurrence profile ha when the adherence of the waterdrop to the humidity detection part 68 occurs at a timing t10 and a change mode in the humidity RH of the non-adherence profile hb when the humidity of the intake air actually changes at the timing t10 for comparison.

In the adherence occurrence profile ha, the adherence of the waterdrop occurs at the timing t10, the adherence of the waterdrop continues until reaching a timing t20, and the waterdrop is eliminated due to drying or the like at the timing t20. In that case, the waterdrop is continuously adhered over an adherence time Ta at the timings t10 to t20. The humidity RH of the adherence occurrence profile ha is held at a relatively large value such as a value close to 100% with the occurrence of the adherence of the waterdrop, but in FIGS. 7 and 8, a holding time is illustrated to be shorter. In FIGS. 7 and 8, a temperature TM also changes before and after the timing t10. In other words, the waterdrop is dried when the waterdrop adhered to the humidity detection part 68 is removed.

As shown in FIG. 7 and FIG. 8, in a rising portion of the adherence occurrence profile ha where the humidity RH increases, the first-order differential value RH1 indicating a rate of change of the humidity RH increases from the timing t10, and the positive and negative are reversed at a timing t13, and the first-order differential value RH1 starts to decrease. At the timing t13, an inflection point IPa of the humidity RH of the adherence occurrence profile ha exists, and the first-order differential value RH1 reaches a maximum value at the timing t13.

In the adherence occurrence profile ha, the second-order differential value RH2 indicating a rate of a change in the rate of change of the humidity increases from the timing t10, and at the timing t12 prior to reaching the timing t13, the positive and negative values are inverted, and the second-order differential value RH2 starts to decrease. The second-order differential value RH2 reaches a maximum value at the timing t12, and then reaches zero at the timing t13 of the inflection point IPa by decreasing. In the present embodiment, the zero is set as the third threshold value Q3.

The present inventors have obtained a knowledge that the humidity RH of the adherence occurrence profile ha changes more abruptly than the humidity RH of the non-adherence profile hb. For example, in a rising portion where the humidity RH increases, the adherence occurrence profile ha increases more sharply than the non-adherence profile hb. According to the above knowledge, the humidity RH increases more sharply as a maximum value of the second-order differential value RH2 increases more. As shown in FIGS. 7 and 8, the maximum value of the second-order differential value RH2 of the adherence occurrence profile ha is larger than the maximum value of the second-order differential value RH2 of the non-adherence profile hb. In that instance, the first threshold value Q1 is set to a value that is difficult to reach in the second-order differential value RH2 of the non-adherence profile hb and reaches as the second-order differential value RH2 of the adherence occurrence profile ha, so that the occurrence of the waterdrop adherence can be detected with the first threshold value Q1 as a determination criterion. The first threshold value Q1 needs to be set to a value larger than the maximum value reachable by the second-order differential value RH2 of the non-adherence profile hb and smaller than the maximum value reachable by the second-order differential value RH2 of the adherence occurrence profile ha.

Further, the present inventors have obtained a knowledge that the second-order differential value RH2 of the adherence occurrence profile ha reaches the third threshold value Q3 earlier than the second-order differential value RH2 of the non-adherence profile hb in the rising portion of the humidity RH. According to the above knowledge, an inflection time Tb required from a time when the second-order differential value RH2 increases to reach the first threshold value Q1 to a time when the second-order differential value RH2 reaches the third threshold value Q3 is shorter in the adherence occurrence profile ha than in the non-adherence profile hb. In FIG. 8, the second-order differential value RH2 reaches the first threshold value Q1 at the timing t11, the timings t11 to t13 are the inflection time Tb of the adherence occurrence profile ha, and the timing t11 to t14 are the inflection time Tb of the non-adherence profile hb. When the first threshold time Tr1 serving as a determination criterion is set for the inflection time Tb, the use of the first threshold time Tr1 can determine whether or not the adherence of the waterdrop has occurred. In that instance, the first threshold time Tr1 needs to be set to a value larger than the maximum time that can be obtained by the inflection time Tb of the adherence occurrence profile ha and smaller than a minimum time that can be obtained by the inflection time Tb of the non-adherence profile hb. The first threshold time corresponds to an occurrence threshold time.

In a falling portion of the adherence occurrence profile ha where the humidity RH decreases, the first-order differential value RH1 of the humidity RH decreases from the timing t20, and starts to increase at a timing t23. At the timing t23, an inflection point IMa of the humidity RH of the adherence occurrence profile ha exists, and the first-order differential value RH1 reaches the minimum value at the timing t23. If the humidity RH is limited to the falling portion of the humidity RH, an absolute value of the first-order differential value RH1 reaches the maximum value at the timing t23.

The second-order differential value RH2 of the adherence occurrence profile ha decreases from the timing t20, and increases at the timing t22 prior to reaching the timing t23. The second-order differential value RH2 reaches the minimum value at the timing t22, and then reaches the third threshold value Q3 at the timing t23 of the inflection point IMa by increasing. An absolute value of the second-order differential value RH2 reaches the maximum value at the timing t22 only in the falling portion of the adherence occurrence profile ha.

In the falling portion where the humidity RH decreases, the adherence occurrence profile ha decreases more sharply than the non-adherence profile hb. According to the above knowledge of the present inventors, the humidity RH decreases more sharply as the minimum value of the second-order differential value RH2 is smaller. As shown in FIGS. 7 and 8, the minimum value of the second-order differential value RH2 of the adherence occurrence profile ha is smaller than the minimum value of the second-order differential value RH2 of the non-adherence profile hb. In that instance, since the second threshold value Q2 is set to a value that is difficult to reach in the second-order differential value RH2 of the non-adherence profile hb and reaches as the second-order differential value RH2 of the adherence occurrence profile ha, the elimination of the waterdrops can be detected with the second threshold value Q2 as a determination criterion. The second threshold value Q2 needs to be set to a value smaller than the minimum value that can be reached by the second-order differential value RH2 of the non-adherence profile hb and larger than the minimum value that can be reached by the second-order differential value RH2 of the adherence occurrence profile ha.

Further, the present inventors have obtained a knowledge that the second-order differential value RH2 of the adherence occurrence profile ha reaches the third threshold value Q3 earlier than the second-order differential value RH2 of the non-adherence profile hb in the falling portion of the humidity RH. According to the above knowledge, similarly to the inflection time Tb, the inflection time Tc required from a time when the second-order differential value RH2 decreases and reaches the second threshold value Q2 to a time when the second-order differential value RH2 reaches the third threshold value Q3 is shorter in the adherence occurrence profile ha than in the non-adherence profile hb. In FIG. 8, the second-order differential value RH2 reaches the second threshold value Q2 at the timing t21, and the timings t21 to t23 are the inflection times Tc of the adherence occurrence profile ha. When the second threshold time Tr2 serving as a determination reference is set for the inflection time Tc, the use of the second threshold time Tr2 can determine whether or not the waterdrop has been eliminated. In that instance, the second threshold time Tr2 needs to be set to a value larger than the maximum time that can be obtained by the inflection time Tc of the adherence occurrence profile ha and smaller than a minimum time that can be obtained by the inflection time Tc of the non-adherence profile hb. The second threshold time Tr2 corresponds to a dry threshold time.

Further, by comparing the first-order differential value RH1 with predetermined threshold values P1 and P2, it can be determined whether or not waterdrops adhere to the humidity detection part 68. More specifically, in the rising portion of the humidity RH, the maximum value of the first-order differential value RH1, which is a rate of change, becomes larger in the adherence occurrence profile ha than in the non-adherence profile hb. The upper threshold value P1 is a threshold value which is set to a positive value, for determining whether or not adherence of waterdrops has occurred. In that instance, the upper threshold value P1 needs to be set to a value larger than the maximum value that can be reached by the first-order differential value RH1 of the non-adherence profile hb, and smaller than the maximum value that can be achieved by the first-order differential value RH1 of the adherence occurrence profile ha.

In the falling portion of the humidity RH, the maximum value of the first-order differential value RH1 is smaller in the adherence occurrence profile ha than in the non-adherence profile hb. A lower threshold value P2 is a threshold value which is set to a negative value, for determining whether or not the waterdrops have been eliminated. In that instance, the lower threshold value P2 needs to be set to a value that is smaller than the minimum value that can be reached by the first-order differential value RH1 of the non-adherence profile hb and larger than the minimum value that can be reached by the first-order differential value of the adherence occurrence profile ha. For example, the lower threshold value P2 is set to a negative value having the same absolute value as that of the upper threshold value P1.

In the signal processing part 44, the waterdrop determination part 73 performs a waterdrop determination process for determining whether or not the waterdrop has adhered to the humidity detection part 68. The waterdrop determination processing is repeatedly performed at a predetermined cycle. This waterdrop determination processing will be described with reference to a flowchart of FIG. 9.

In the signal processing part 44, the threshold value setting part 74 sets the threshold values Q1 to Q3 and the threshold time Tr1, Tr2 based on the environmental information and the vehicle information. For example, when the responsiveness of the humidity detection part 68 or the like is lowered due to aging deterioration or the like, there is a possibility that the steepness of the change of the humidity RH calculated by the measurement value calculation part 72 becomes gradual. Therefore, it is assumed that the responsiveness of the humidity detection part 68 and the like tends to decrease as the cumulative travel distance in the vehicle information increases, and the first threshold value Q1 is set to a smaller value and the third threshold value Q3 is set to a larger value as the cumulative travel distance increases more. As a result, the occurrence of a situation in which the second-order differential value RH2 of the humidity RH does not reach the threshold values Q1 and Q3 despite the occurrence of the adherence of waterdrops to the humidity detection part 68 is inhibited due to the aging of the humidity detection part 68. The threshold value setting part 74 first sets a positive value calculated based on the environment information and the vehicle information as the first threshold value Q1, and sets the second threshold value Q2 according to the first threshold value Q1. For example, a negative value having the same absolute value as the first threshold value Q1 is set as the second threshold value Q2.

Figure 9:
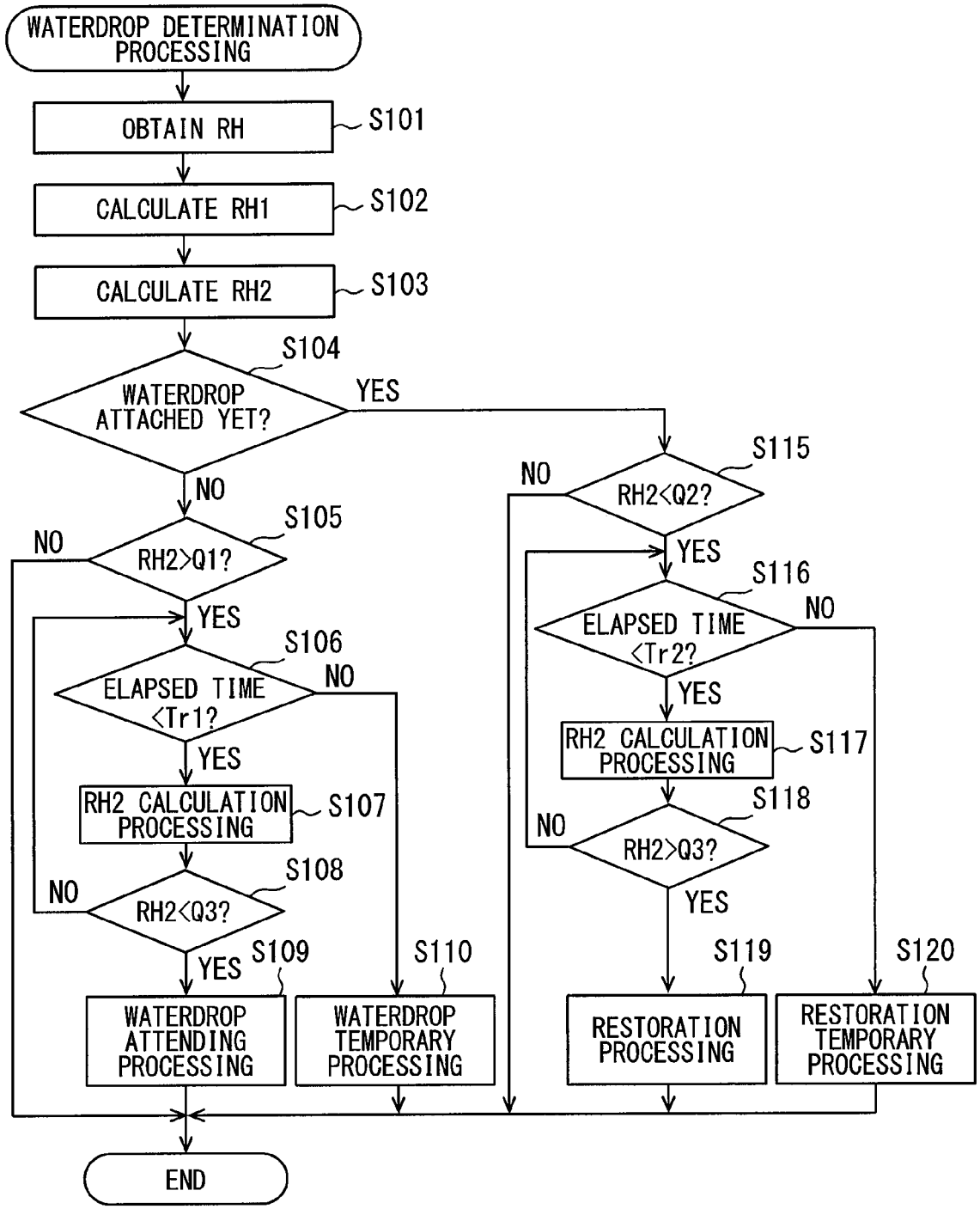
FIG. 9 is a flowchart showing a procedure of a waterdrop determination process.

In FIG. 9, in Step S101, the humidity RH calculated by the measurement value calculation part 72 is obtained. In Step S102, the first-order differential value RH1 is calculated by performing the first-order differentiation on the humidity RH, and in Step S103, the second-order differential value RH2 is calculated by performing the second-order differentiation on the humidity RH. In Step S104, it is determined whether or not the waterdrop has adhered to the humidity detection part 68. For example, it is determined whether or not a flag indicating that the adherence of the waterdrop has already occurred is set in the storage circuit 70 or the like. When it is determined that the waterdrop is not adhered, the process proceeds to Step S105 in order to determine whether or not the waterdrop has adhered to the humidity detection part 68.

In Step S105, it is determined whether or not the second-order differential value RH2 becomes larger than the first threshold value Q1. If the waterdrop does not become larger, the waterdrop determination processing is terminated because no waterdrop has adhered to the humidity detection part 68. If the waterdrop size becomes larger, the process proceeds to Step S106 on the assumption that there is a possibility that the adherence of the waterdrop has occurred. The function of executing the processing of Step S105 corresponds to an adherence determination part and an occurrence determination part. For example, in the case of the humidity RH of the adherence occurrence profile ha shown in FIGS. 7 and 8, the determination of Step S105 is affirmed at the timing t11 at which the second-order differential value increases to reach the first threshold value Q1, and the process proceeds to Step S106.

In Step S106 to S108, it is determined whether or not the second-order differential value RH2 has become smaller than the third threshold value Q immediately after the second-order differential value RH2 has become larger than the first threshold value Q1. More specifically, in Step S106, it is determined whether or not an elapsed time from a time when the second-order differential value RH2 becomes larger than the first threshold value Q1 is still shorter than the first threshold time Tr1. If the elapsed time has not already been shorter than the first threshold time Tr1, it is determined that the second-order differential value RH2 is not rapidly decreased, and the process proceeds to Step S110. The function of executing the processing of Step S106 corresponds to an adherence determination part and an occurrence time determination part.

When the elapsed time is still shorter than the first threshold time Tr1, the process proceeds to Step S107, where the humidity RH is obtained and the second-order differential value RH2 is calculated in the same manner as in Step S101 and S103. The function of executing the processing of Steps S103 and S107 corresponds to a second-order calculation part. In Step S108, it is determined whether or not the second-order differential value RH2 calculated in Step S107 becomes smaller than the third threshold value Q3. When the second-order differential value RH2 is not smaller than the third threshold value Q3, the processing of Step S106 to S108 is repeated until the elapsed time reaches the first threshold time Tr1. The function of executing Step S108 corresponds to an adherence determination part and an occurrence inflection determination part.

When the second-order differential value RH2 becomes smaller than the third threshold value Q3 in a stage where the elapsed time does not reach the first threshold time Tr1, it is determined that the adherence of the waterdrop to the humidity detection part 68 has occurred, and the process proceeds to Step S109. In Step S109, waterdrop attending processing is performed as a countermeasure against the occurrence of the waterdrop adherence. In the waterdrop attending processing, for example, fail-safe processing is performed. In the fail-safe processing, the substitute humidity as fail-safe data is read out from the storage circuit 70, and the substitute humidity is included in the humidity information to be outputted to the ECU 15 in place of the humidity RH calculated by the measurement value calculation part 72. This fail-safe processing is continued until there is no waterdrop adhered to the humidity detection part 68.

The substitute humidity is a predetermined value such as 80% RH, for example, which is previously stored in the storage circuit 70. The substitute humidity may be a value that is set every time according to the situation at that time. In other words, the substitute humidity is not necessarily the predetermined value. For example, the humidity RH in the past for a predetermined time (for example, 1 minute) may be used as the substitute humidity based on a timing at which the second-order differential value RH2 becomes larger than the first threshold value Q1. The past humidity RH is stored in the storage circuit 70, and is read out from the storage circuit 70. It is considered that the possibility that the substitute humidity is greatly different from the current actual humidity is low.

In Step S109, processing of setting a flag indicating that the waterdrops have adhered to the humidity detection part 68 in the storage circuit 70 or the like is also performed. With the execution of the above processing, an affirmation is made in the determination of Step S104 when the waterdrops have already adhered. In the case of, for example, the humidity RH of the adherence occurrence profile ha shown in FIGS. 7 and 8, affirmation is made in the determination of Step S108 at the timing t13 at which the second-order differential value RH2 decreases and reaches the third threshold value Q3, and the process proceeds to Step S109.

On the other hand, if the second-order differential value RH2 does not fall below the third threshold value Q3 before the elapsed time reaches the first threshold time Tr1, the process proceeds to Step S110 and performs waterdrop temporary processing as there is a possibility that the waterdrops may not have adhered. In this example, it is assumed that, for example, the first threshold value Q1 is too small as an example of the reason why the second-order differential value RH2 does not become smaller than the third threshold value Q3 within the first threshold time Tr1 even though the second-order differential value RH2 becomes larger than the first threshold value Q1. In that instance, even though no waterdrop has adhered to the humidity detection part 68, the second-order differential value RH2 becomes larger than the first threshold value Q1 due to an actual humidity change.

Therefore, as the waterdrop temporary processing, the threshold value setting part 74 is caused to perform processing of updating the first threshold value Q1 to a value larger by a predetermined value. As a result, the second-order differential value RH2 is avoided from becomes a value larger than the first threshold value Q1 even though no waterdrop has adhered to the humidity detection part 68. The predetermined value is, for example, a value of several percent of the first threshold value Q1, and is stored in advance in the storage circuit 70. After the waterdrop temporary processing, it is determined that waterdrop adherence to the humidity detection part 68 has not occurred, and the waterdrop determination processing is terminated.

If it is determined in Step S104 that waterdrops have already been adhered to the humidity detection part 68, the process proceeds to Step S115 to determine whether or not the adhered waterdrops are no longer present. In Step S115, it is determined whether or not the second-order differential value RH2 becomes smaller than the second threshold value Q2. If the waterdrops have not been reduced, the present waterdrop determination processing is terminated because the waterdrops are not lost, and if the waterdrops have been reduced, it is considered that there is a possibility that the waterdrops are lost, and the process proceeds to Step S116. The function of executing the processing of Step S115 corresponds to an adherence determination part and a dry determination part. In the case of, for example, the humidity RH of the adherence occurrence profile ha shown in FIGS. 7 and 8, the determination of Step S115 is affirmed at the timing t21 at which the second-order differential value RH2 decreases and reaches the second threshold value Q2, and the process proceeds to Step S116.

In Steps S116 to S118, it is determined whether or not the second-order differential value RH2 has become smaller than the second threshold value Q2 and then quickly becomes larger than the third threshold value Q3. Specifically, in Step S116, it is determined whether or not the elapsed time after the second-order differential value RH2 becomes smaller than the second threshold value Q2 is still shorter than the second threshold time Tr2. If the elapsed time is not shorter than the second threshold time Tr2, it is determined that the second-order differential value RH2 is not rapidly decreased, and the process proceeds to Step S120. The function of executing the processing of Step S116 corresponds to an adherence determination part and a drying time determination part.

When the elapsed time is still shorter than the second threshold time Tr2, the process proceeds to Step S117, where the humidity RH is obtained and the second-order differential value RH2 is calculated in the same manner as in Step S107. The function of executing the process of Step S117 corresponds to a second-order calculation part. In Step S118, it is determined whether or not the second-order differential value RH2 calculated in Step S117 becomes larger than the third threshold value Q3. If the second-order differential value RH2 is not larger than the third threshold value Q3, the processing of Step S116 to S118 is repeated until the elapsed time reaches the second threshold time Tr2. The function of executing the processing of Step S118 corresponds to an adherence determination part and a dry inflection determination part.

When the second-order differential value RH2 becomes larger than the third threshold value Q3 in a stage where the elapsed time does not reach the second threshold time Tr2, it is determined that the adherence of the waterdrop to the humidity detection part 68 has occurred, and the process proceeds to Step S119. In Step S119, restoration processing for terminating the waterdrop attending processing such as the fail-safe processing is performed. In the restoration processing, the humidity information output to the ECU 15 is not included in the substitute humidity information, but the humidity RH calculated by the measurement value calculation part 72 is included in the humidity information. As a result, the ECU 15 controls the operation of the internal combustion engine 11 in accordance with each humidity RH.

On the other hand, if the second-order differential value RH2 does not become larger than the third threshold value Q3 before the elapsed time reaches the second threshold time Tr2, it is considered that there is a possibility that the waterdrop is not lost, and the process proceeds to Step S120, and restoration temporary processing is performed. In this example, it is assumed that, for example, the second threshold value Q2 is too large as an example of the reason why the second-order differential value RH2 does not become larger than the third threshold value Q3 within the second threshold time Tr2 despite that the second-order differential value RH2 becomes smaller than the second threshold value Q2. In that instance, the second-order differential value RH2 becomes smaller than the second threshold value Q2 due to an error or the like in the humidity RH, even though the waterdrops adhered to the humidity detection part 68 are not completely eliminated.

Therefore, the threshold value setting part 74 is caused to perform processing of updating the second threshold value Q2 to a value smaller by a predetermined value as the restoration temporary processing. This prevents the second-order differential value RH2 from becoming smaller than the second threshold value Q2 even though the waterdrop is not eliminated. The predetermined value is, for example, a value of several percent of the second threshold value Q2, and is stored in advance in the storage circuit 70. Further, after the restoration temporary processing, it is determined that no waterdrops are eliminated, and the present waterdrop determination processing is terminated.

The determination as to whether or not the waterdrop has adhered to the humidity detection part 68 may be considered to be a determination as to whether or not an abnormality occurs in which the waterdrop has adhered to the humidity detection part 68. In that case, the signal processing part 44 may also be referred to as an abnormality detection device that detects whether or not an abnormality has occurred in the humidity detection part 68.

According to the present embodiment described above, since the second-order differential value RH2 of the humidity RH is used to determine whether or not the waterdrop has adhered to the humidity detection part 68, there is no need to wait until a time when the humidity RH is held at a value close to 100% is measured. In addition, the second-order differential value RH2 requires a shorter time to reach the maximum value due to the occurrence of adherence of the waterdrop, and a shorter time to reach the minimum value due to the elimination of the adhered waterdrop, than those in the first-order differential value RH1. This also makes it possible to improve the responsiveness of the determination as to the adherence of the waterdrop to the humidity detection part 68 while maintaining the proper determination accuracy.

As shown in FIGS. 7 and 8, when the adherence of the waterdrop to the humidity detection part 68 occurs, the timing t12 at which the second-order differential value RH2 reaches the maximum value is earlier than the timing t13 at which the first-order differential value RH1 reaches the maximum value in the rising portion of the humidity RH. This is because the first-order differential value RH1 reaches the maximum value at an inflection point IPa of the humidity RH, whereas the second-order differential value RH2 reaches the maximum value at a stage prior to the inflection point IPa of the humidity RH. For that reason, in the configuration in which the determination as to whether or not the adherence of the waterdrop has occurred is performed with the use of the second-order differential value RH2 as in the present embodiment, the occurrence of the adherence of the waterdrop can be grasped at an earlier timing than the configuration in which the adherence of the waterdrop is performed with the use of the first-order differential value RH1.

Similarly, when the adhered waterdrop is eliminated, the timing t22 at which the second-order differential value RH2 reaches the minimum value is earlier than the timing t23 at which the first-order differential value RH1 reaches the minimum value at a falling portion of the humidity RH. This is because the first-order differential value RH1 reaches the minimum value at an inflection point IMa of the humidity RH, whereas the second-order differential value RH2 reaches the minimum value at a stage prior to the inflection point IMa of the humidity RH. For that reason, in the configuration in which the determination as to whether or not the waterdrops have been eliminated is performed with the use of the second-order differential value RH2 as in the present embodiment, the elimination of the waterdrops can be grasped at an earlier timing than the configuration in which the determination is performed with the use of the first-order differential value RH1.

According to the present embodiment, whether or not the second-order differential value RH2 is larger than the first threshold value Q1 is determined, thereby being capable of grasping that the waterdrops have adhered to the humidity detection part 68. In addition, the first threshold value Q1 is set to a small value that is hardly reached by the second-order differential value RH2 of the humidity RH when the adherence of the waterdrops does not occur, such as the non-adherence profile hb. For that reason, a situation can be inhibited in which the adherence of the waterdrops to the humidity detection part 68 does not occur even though the second-order differential value RH2 becomes larger than the first threshold value Q1.

When an abnormality occurs in the humidity detection part 68 or the like, or when the waterdrop is not actually adhered to the humidity detection part 68, the second-order differential value RH2 does not necessarily reach the first threshold value Q1. On the other hand, according to the present embodiment, even if the second-order differential value RH2 is increased to the first threshold value Q1, it is determined whether the second-order differential value RH2 is decreased to the third threshold value Q3, so that erroneous determination of the occurrence of waterdrop adherence to the humidity detection part 68 is inhibited. Therefore, the accuracy of the determination as to whether or not the adherence of the waterdrops to the humidity detection part 68 has occurred can be enhanced.

According to the present embodiment, it is determined whether or not the second-order differential value RH2 has increased to the first threshold value Q1 and then decreased to the third threshold value Q3 within the first threshold time Tr1. For that reason, even if the second-order differential value RH2 increases to the first threshold value Q1 even though no waterdrop has adhered to the humidity detection part 68, erroneous determination that the waterdrop has adhered to the humidity detection part 68 is inhibited. This is because it is difficult for the second-order differential value RH2 to be decreased to the third threshold value Q3 within the first threshold time Tr1 when no waterdrop has adhered.

According to the present embodiment, after the adherence of the waterdrop to the humidity detection part 68 has occurred, it is determined whether or not the second-order differential value RH2 becomes smaller than the second threshold value Q2, thereby making it possible to recognize that the adhered waterdrop is no longer present. Moreover, the second threshold value Q2 is set to a value that is unlikely to be reached by the second-order differential value RH2 of the humidity RH when the adherence of the waterdrop does not occur, such as the non-adherence profile hb. This makes it possible to inhibit a situation in which the waterdrop is not eliminated even though the second-order differential value RH2 becomes smaller than the second threshold value Q2.

The second-order differential value RH2 does not necessarily reach the second threshold value Q2 when an abnormality occurs in the humidity detection part 68 or the like, or when the waterdrop adhered to the humidity detection part 68 is not actually eliminated, or the like. On the other hand, according to the present embodiment, since it is determined whether or not the second-order differential value RH2 increases to the third threshold value Q3 even if the second-order differential value RH2 decreases to the second threshold value Q2, erroneous determination of the elimination of the adhered waterdrops is inhibited. Therefore, the accuracy of the determination as to whether or not the waterdrop adhered to the humidity detection part 68 has been eliminated can be enhanced.

According to the present embodiment, it is determined whether or not the second-order differential value RH2 has decreased to the second threshold value Q2 and then increased to the third threshold value Q3 within the second threshold time Tr2. For that reason, even if the second-order differential value RH2 decreases to the second threshold value Q2 even though the waterdrop adhered to the humidity detection part 68 is not eliminated, erroneous determination that the waterdrop is not eliminated is inhibited. This is because the second-order differential value RH2 does not easily increase to the third threshold value Q3 within the second threshold time Tr2 when the waterdrop is not eliminated.

According to the present embodiment, the signal processing part 44 of the air flow meter 14 includes both of the measurement value calculation part 72 and the waterdrop determination part 73. For that reason, the humidity information including the humidity RH calculated by the measurement value calculation part 72 does not need to be supplied to the outside of the air flow meter 14 before the humidity information is used for the determination by the waterdrop determination part 73. In addition, since the signal processing part 44 has the storage circuit 70, there is no need to output various pieces of information read out from the storage circuit 70 to the outside of the air flow meter 14 before the waterdrop determination part 73 uses the information for determination. As a result, the possibility of noise such as disturbance entering into various types of information used for the determination by the waterdrop determination part 73 can be reduced. Therefore, the accuracy of the respective determinations as to whether or not the adherence of the waterdrop to the humidity detection part 68 has occurred, and whether or not the adhered waterdrop has been eliminated can be enhanced.

According to the present embodiment, the humidity detection part 68 is included in the air flow meter 14. For that reason, the humidity RH, which is the detection result of the humidity detection part 68, can be output to the ECU 15 through the connecting line connected to the connector part 49 together with the flow rate, which is the detection result of the flow rate detection part 42, and the temperature, which is the detection result of the temperature detection part 67. As described above, the humidity detection function, the flow rate detection function, and the temperature detection function are integrated into the air flow meter 14, thereby being capable of achieving a reduction in the number of connection lines as compared with a configuration in which, for example, the humidity detection part 68 is provided separately from the air flow meter 14. In addition, since the connector part 49 and the like can be shared by the humidity detection part 68, the flow rate detection part 42, and the temperature detection part 67, a cost reduction can be achieved.

Second Embodiment

In the first embodiment, only the second-order differential value RH2 of the humidity RH is used to determine whether or not the waterdrop has adhered to the humidity detection part 68, but the first-order differential value RH1 and the second-order differential value RH2 may be combined together in use. In the second embodiment, as shown in FIG. 10, a first-order differential value RH1 is used for both of a determination of whether or not the adherence of a waterdrop to a humidity detection part 68 has occurred and a determination of whether or not the waterdrop adhered to the humidity detection part 68 has been eliminated.

Figure 10:
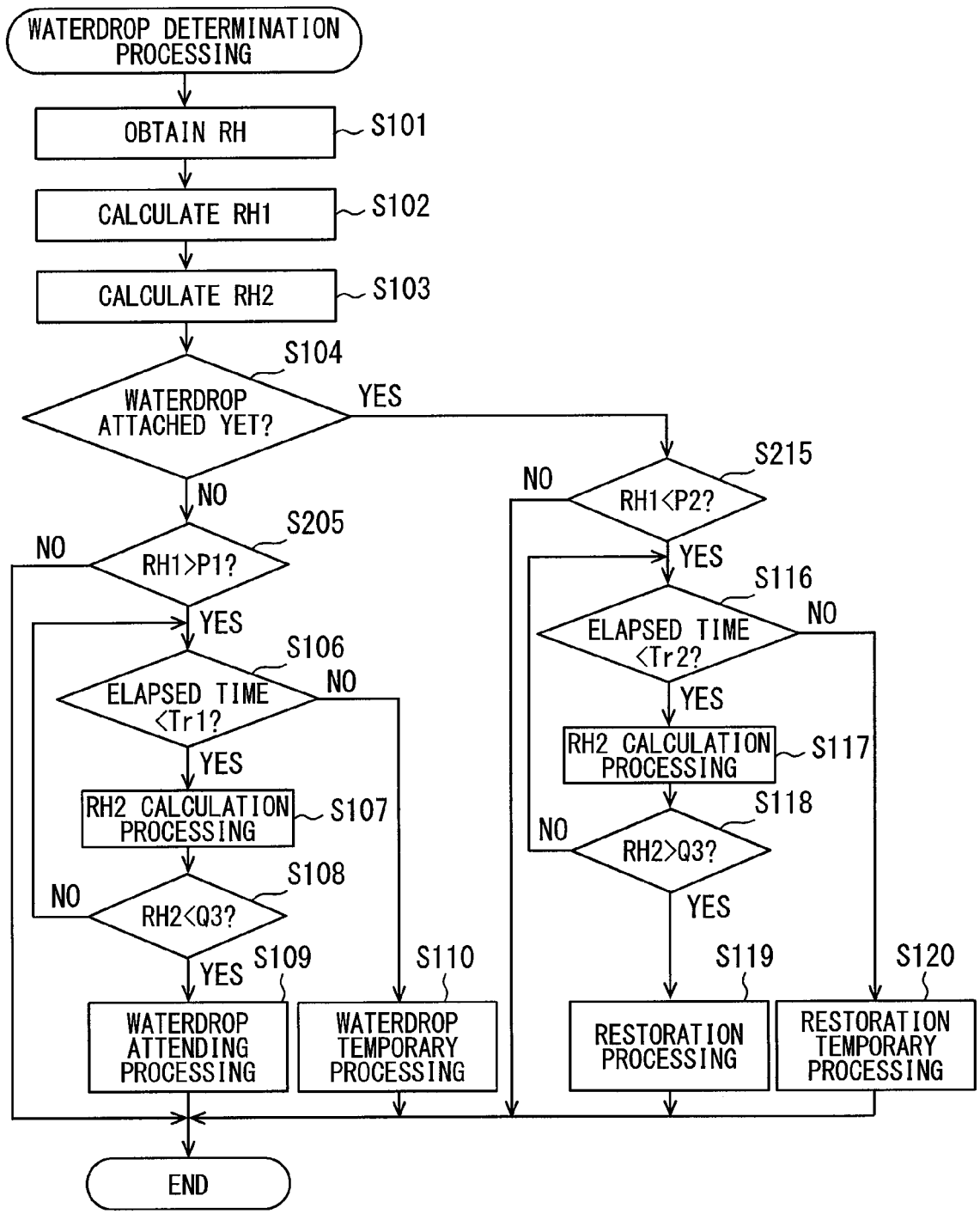
FIG. 10 is a flowchart showing a procedure of a waterdrop determination process according to a second embodiment.

In FIG. 10, Steps S205 and S215 are executed instead of Steps S105 and S115 of the first embodiment. In Step S205, it is determined whether or not the first-order differential value RH1 of the humidity RH becomes larger than an upper threshold value P1. As described above, the upper threshold value P1 is set to a value larger than a maximum value reachable by the first-order differential value RH1 of a non-adherence profile hb shown in FIG. 7 and smaller than a maximum value reachable by the first-order differential value RH1 of an adherence occurrence profile ha. For that reason, when the first-order differential value RH1 becomes larger than the upper threshold value P1, it is determined that there is a possibility that the adherence of the waterdrop has occurred, and the process proceeds to Step S106. On the other hand, if the first-order differential value RH1 is not large than the upper threshold value P1, it is determined that the adherence of the waterdrop has not occurred, and the present waterdrop determination processing is terminated.

Here, in the rising portion of the humidity RH, as shown in FIG. 7, after the second-order differential value RH2 has reached the maximum value, the first-order differential value RH1 reaches the maximum value, and the second-order differential value RH2 decreases to the third threshold value Q3. For that reason, if the upper threshold value P1 is set to a value smaller than the maximum value of the first-order differential value RH1, the second-order differential value RH2 decreases to the third threshold value Q3 after the first-order differential value RH1 increases to the upper threshold value P1. Therefore, even when Step S205 is executed instead of Step S105, the determination accuracy of whether or not the waterdrop has been adhered can be enhanced by determining whether or not the second-order differential value RH2 has become larger than the first threshold value Q1 in Step S106.

With respect to the falling portion of the humidity RH, as shown in FIG. 7, after the second-order differential value RH2 has reached the minimum value, the first-order differential value RH1 reaches the minimum value and the second-order differential value RH2 decreases to the third threshold value Q3. For that reason, if the lower threshold value P2 is set to a value larger than the minimum value of the first-order differential value RH1, the second-order differential value RH2 increases to the third threshold value Q3 after the first-order differential value RH1 has decreased to the lower threshold value P2. Therefore, even when Step S215 is executed instead of Step S115, whether or not the second-order differential value RH2 becomes smaller than the second threshold value Q2 is determined in Step S116, thereby being capable of improving the determination accuracy of whether or not the waterdrop adhered to the humidity detection part 68 has been eliminated.

Third Embodiment

In the first embodiment described above, the determination of whether or not the waterdrop has adhered to the humidity detection part 68 is performed by the signal processing part 44 of the air flow meter 14, but in a third embodiment, the determination is performed by an ECU 15. In that instance, the ECU 15, which is a control device of the internal combustion engine 11, performs waterdrop determination processing.

Figure 11:
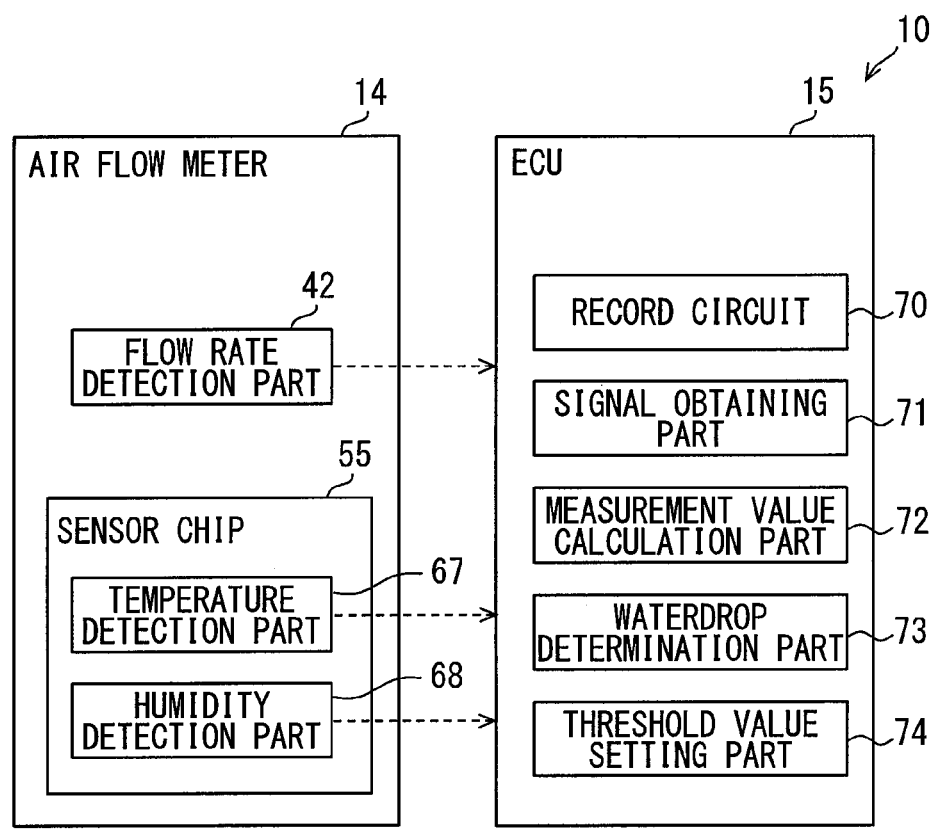
FIG. 11 is a block diagram showing an electrical configuration of a control system according to a third embodiment.

In the present embodiment, as shown in FIG. 11, the ECU 15, instead of the air flow meter 14, includes a storage circuit 70, a signal obtaining part 71, a measurement value calculation part 72, a waterdrop determination part 73, and a threshold value setting part 74. In the above configuration, the air flow meter 14 does not have a signal processing part 44, and various signals of a flow rate detection part 42, a temperature detection part 67, and a humidity detection part 68 are input to the ECU 15 without passing through the signal processing part 44. In addition to the signals from the detection parts 42, 67, and 68, various signals are input to the ECU 15 from measuring parts such as an intake air temperature sensor 25 and so on. The ECU 15 calculates various numerical values by the measurement value calculation part 72 based on various types of signals input from the measuring part, and uses those numerical values as parameters to perform an engine control such as adjusting the opening degree of the throttle valve 21.

The ECU 15 performs parameter processing for setting the humidity RH measured with the use of a detection signal from the humidity detection part 68 to one of the parameters for performing the engine control. The above parameter processing is repeatedly performed in a predetermined cycle. The above parameter processing will be described with reference to a flowchart of FIG. 12.

Figure 12:
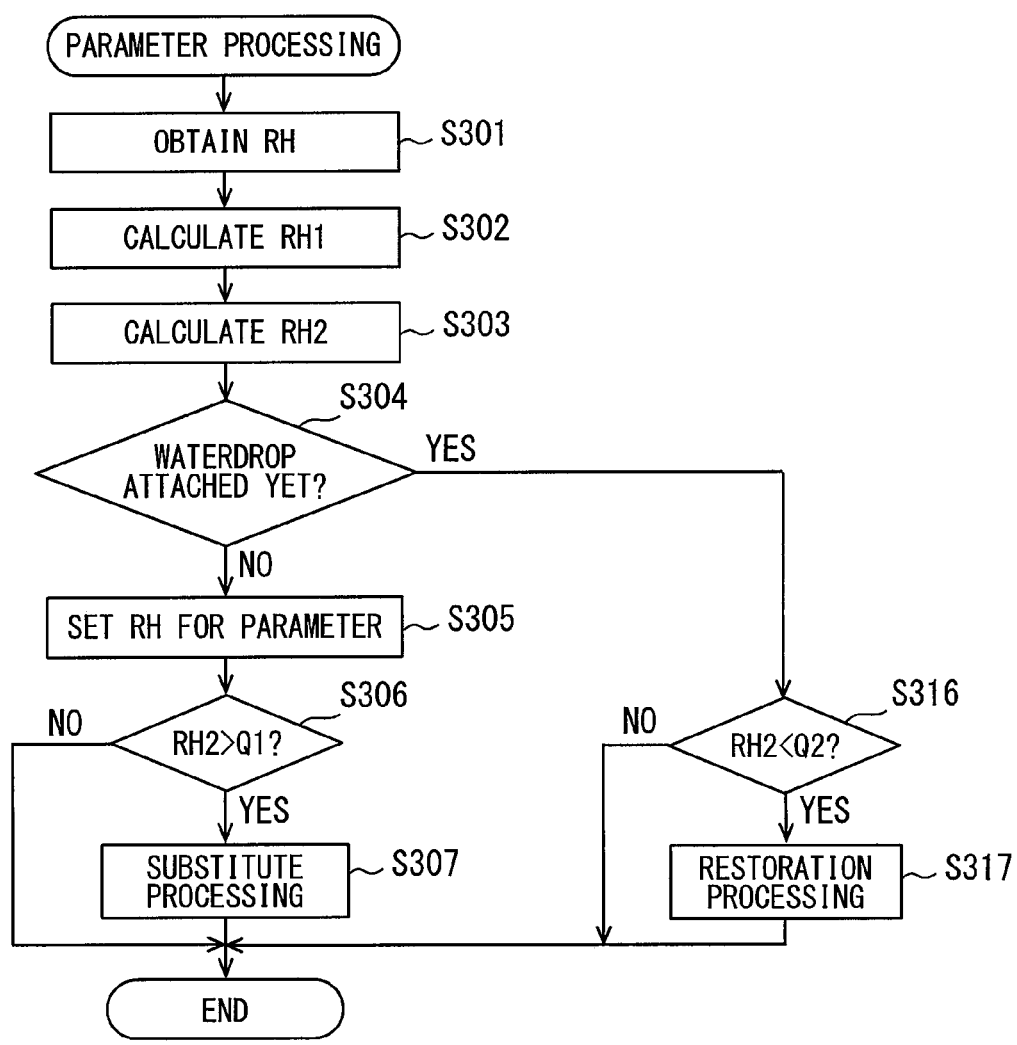
FIG. 12 is a flowchart showing a procedure of an engine control process.

In FIG. 12, Step S301 to S304 performs the same processing as that in Step S101 to S104 according to the first embodiment. In this example, Step S301 does not obtain the humidity RH calculated by the measurement value calculation part 72, but calculates the humidity RH based on the humidity signal input from the humidity detection part 68. In that instance, the measurement value calculation part 72 executes Step S301, and the function of executing the processing of Step S301 corresponds to a humidity obtaining part. The function of executing the processing of Step S303 corresponds to a second-order calculation part.

If it is determined in Step S304 that no waterdrop has adhered to the humidity detection part 68, the process proceeds to Step S305, and the humidity RH is set as one of the parameters for controlling the engine. The above processing is performed so that the humidity RH of each time is reflected in the content of the engine control. The function of executing the processing of Step S305 corresponds to a parameter setting part.

In Step S306, similarly to Step S105 of the above embodiment, it is determined whether or not the second-order differential value RH2 is larger than the first threshold value Q1. The function of executing the processing of Step S306 corresponds to an adherence determination part. In addition, even if the same processing as that in Step S107 and S108 according to the first embodiment is not performed, whether or not the second-order differential value RH2 has increased to the first threshold value Q1 is simply determined, thereby determining whether or not the waterdrop has been adhered to the humidity detection part 68. When the second-order differential value RH2 is not larger than the first threshold value Q1, it is determined that waterdrop adherence has not occurred, and the present parameter process is terminated. On the other hand, when the second-order differential value RH2 becomes larger than the first threshold value Q1, it is determined that the waterdrop adherence has occurred, and the process proceeds to Step S307.

In Step S307, substitute processing is performed. In the substitute processing, as in Step S109 of the first embodiment, a substitute humidity is set as one of the parameters for controlling the engine instead of the humidity RH calculated in Step S101. Similar to the first embodiment, a substitute humidity has a predetermined value and is stored in the storage circuit 70 as fail-safe data. Further, the humidity RH in the past for a predetermined period of time may be used as the substitute humidity based on a timing at which the second-order differential value RH2 becomes larger than the first threshold value Q1. In that case, since it is considered that the possibility that the substitute humidity is greatly different from the actual humidity at present is low, the operation state and the fuel consumption of the internal combustion engine 11 can be inhibited from being extremely deteriorated in the engine control executed with the substitute humidity as one of the parameters. The function of executing the processing of Step S307 corresponds to a substitute setting part.

If it is determined in Step S304 that waterdrop has been already adhered to the humidity detection part 68, the process proceeds to Step S316 to determine whether or not the adhered waterdrop is no longer present. In Step S316, similarly to Step S115 of the first embodiment, it is determined whether or not the second-order differential value RH2 is smaller than the second threshold value Q2. If the second-order differential value RH2 is not smaller than the second threshold value Q2, the parameter processing is terminated because it is determined that the waterdrop has not been eliminated, and if the second-order differential value RH2 is smaller than the second threshold value Q2, it is determined that the waterdrop has been eliminated, and the process proceeds to Step S317. The function of executing the processing of Step S316 corresponds to an adherence determination part.

In Step S317, restoration processing is performed in the same manner as in Step S119 of the first embodiment. In the restoration processing, the substitute processing is terminated, the humidity RH is set to one of the parameters for engine control each time, instead of the substitute humidity. As a result, the engine control is performed with the use of the humidity RH at each time.

In the parameter processing, the processing of Steps S301 to S304, S306, and S316 corresponds to waterdrop determination processing. The function of executing the waterdrop determination processing in the ECU 15 corresponds to a humidity measurement device. The ECU 15 corresponds not only to a control device but also to a humidity measurement device and an abnormality detection device.

According to the present embodiment, the ECU 15 includes a measurement value calculation part 72, a waterdrop determination part 73, and the like. For that reason, unlike the configuration in which the air flow meter 14 includes the measurement value calculation part 72 and the waterdrop determination part 73, there is no need to add an electronic circuit such as the signal processing part 44 to the air flow meter 14 as a control device. In the ECU 15, the functions of the measurement value calculation part 72, the waterdrop determination part 73, and the like can be easily added by additionally storing various programs in the storage circuit 70, so that an increase in the cost load can be reduced. In addition, since the ECU 15 has the storage circuit 70, various information read from the storage circuit 70 need not be output to the outside of the ECU 15 before the data is used for the determination by the waterdrop determination part 73. For that reason, the possibility that noise such as disturbance enters various information used for the determination by the waterdrop determination part 73 can be reduced. Therefore, the accuracy of the respective determinations as to whether or not the adherence of the waterdrop to the humidity detection part 68 has occurred, and whether or not the adhered waterdrop has been eliminated can be enhanced.

Other Embodiments

Although a plurality of embodiments according to the present disclosure have been described above, the present disclosure is not construed as being limited to the above-mentioned embodiments, and can be applied to various embodiments and combinations within a scope not departing from the spirit of the present disclosure.

Figure 13:
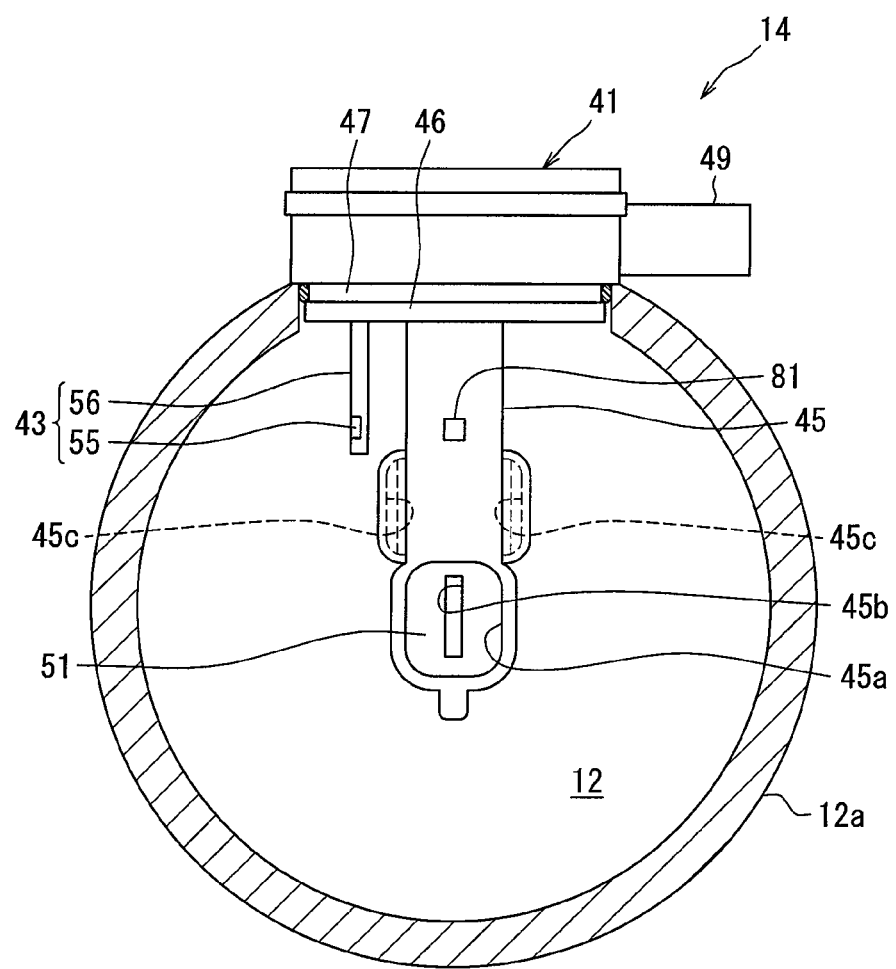
FIG. 13 is a front view of an air flow meter in a state of being adhered to an intake pipe in Modification 1.

As Modification 1, in the first embodiment, the air flow meter 14 may include another temperature detection part 81 in addition to the temperature detection part 67. When those temperature detection parts 67 and 81 are referred to a first temperature detection part 67 and a second temperature detection part 81, respectively, the second temperature detection part 81 has the same configuration as that of the first temperature detection part 67, and is located at the upstream side end portion of the housing 41, for example, as shown in FIG. 13. When it is determined in the waterdrop determination process that no waterdrop has adhered to the humidity detection part 68, the signal processing part 44 calculates the temperature with the use of the temperature signal of the first temperature detection part 67, and outputs the temperature information corresponding to the temperature information to the ECU 15. On the other hand, when it is determined that waterdrop has adhered to the humidity detection part 68, it is determined that the waterdrop is also adhered to the temperature detection part 67, the temperature is calculated with the use of the temperature signal of the second temperature detection part 81, and the temperature information corresponding to the temperature is output to the ECU 15. In other words, in the engine control by the ECU 15, not the detection value of the first temperature detection part 67, but the detection value of the second temperature detection part 91 is set as a parameter.

In the first embodiment, as described above, both of the first temperature detection part 67 and the humidity detection part 68 are formed on one chip substrate 61 in the sensor unit 43. For that reason, when the waterdrop has adhered to the chip substrate 61, it is considered that there is a high possibility that the waterdrop is put across the first temperature detection part 67 and the humidity detection part 68.

In addition, it may be determined whether or not the waterdrop has been adhered to the first temperature detection part 67 based on a change mode of the temperature calculated based on the detection signal from the first temperature detection part 67.

Figure 14:
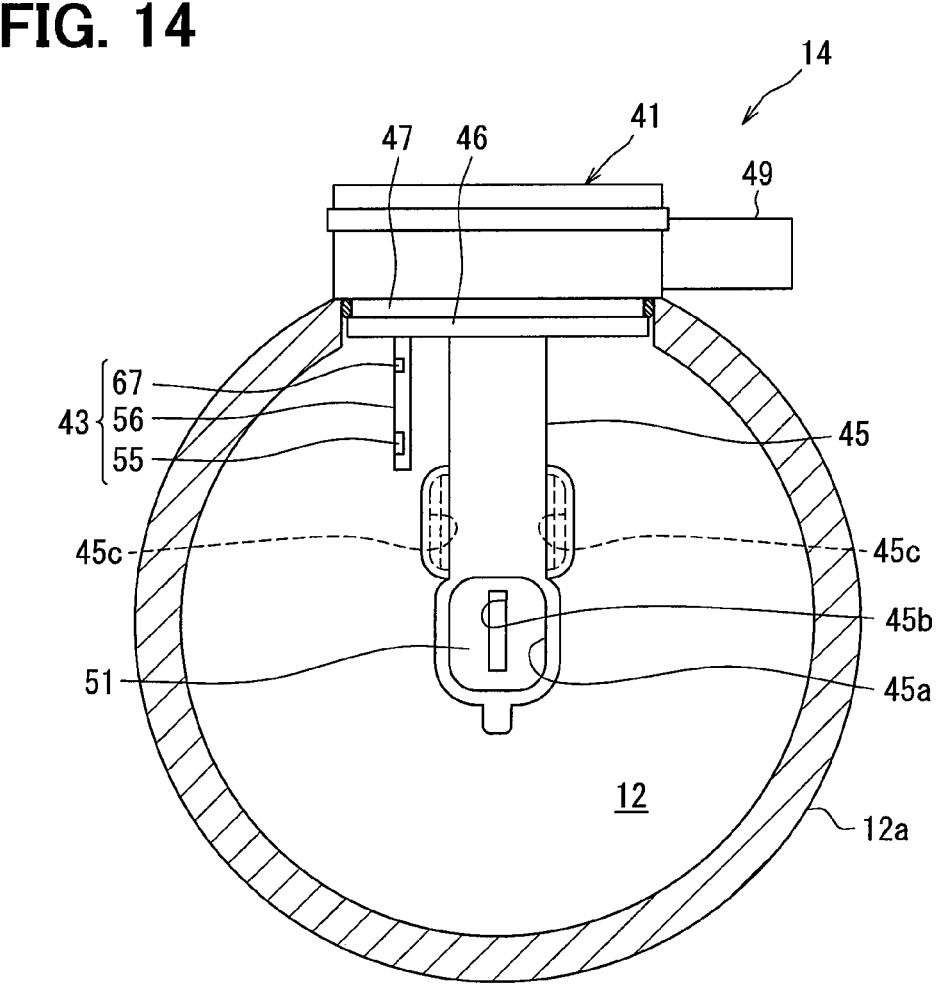
FIG. 14 is a front view of an air flow meter in a state of being adhered to an intake pipe in Modification 2.
Figure 15:
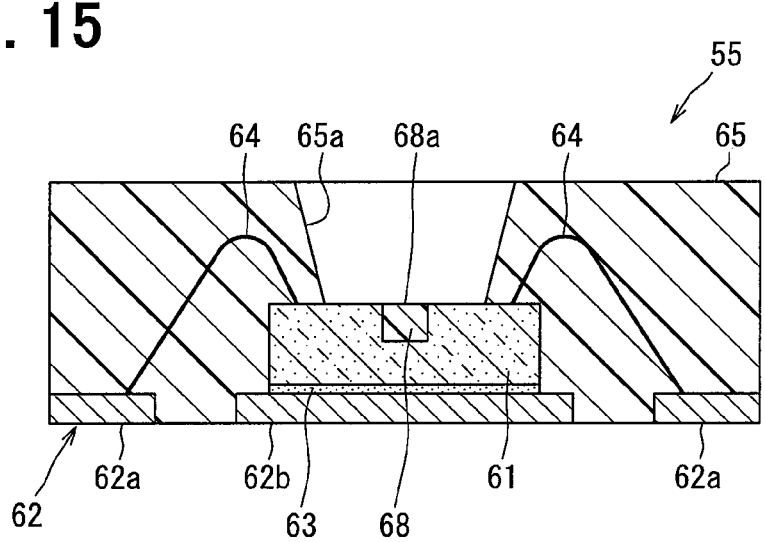
FIG. 15 is a vertical cross-sectional view of the sensor chip.

As Modification 2, in the air flow meter 14 according to the first embodiment, the temperature detection part 67 and the humidity detection part 68 may not be provided in one sensor chip 55. For example, as shown in FIGS. 14 and 15, only the humidity detection part 68 is provided on the chip substrate 61 of the sensor chip 55, and the temperature detection part 67 is located at a position different from that of the sensor chip 55 in the chip support 56. In that case, the sensor unit 43 has the temperature detection part 67 in a state independent of the sensor chip 55.

As Modification 3, in the second-order differential value RH2 according to the first embodiment, a determination criterion for confirming that waterdrop has been adhered to the humidity detection part 68 and a determination criterion for confirming that the waterdrop has been eliminated may be set to values which are not the third threshold value Q3. For example, in Step S108 after the second-order differential value RH2 becomes larger than the first threshold value Q1, the determination criterion is set to a positive value larger than zero, and it is determined whether or not the second-order differential value RH2 has decreased to the positive value. In Step S118 after the second-order differential value RH2 becomes smaller than the second threshold value Q2, the determination criterion is set to a negative value smaller than zero, and it is determined whether or not the second-order differential value RH2 has increased to the negative value.

As Modification 4, the measurement value calculation part 72 of the signal processing part 44 may not calculate the humidity RH in the first to third embodiments. In this example, the humidity signal from the humidity detection part 68 may be subjected to second-order differentiation by time to calculate a second-order differential value. Alternatively, the humidity signal may be simply converted into a numerical value, and the numerical value may be subjected to second-order differentiation by time to calculate a second-order differential value. Even in those cases, the first to third threshold values, the first threshold time, and the second threshold time are set for the second-order differential value, thereby being configured to determine whether or not the second-order differential value has reached those threshold values. In other words, the occurrence threshold value, the dry threshold value, the occurrence inflection value, the dry inflection value, the occurrence threshold time, and the dry threshold time are set for the second-order differential value, thereby being configured to determine whether or not the waterdrop has been adhered to the humidity detection part 68.

As Modification 5, in the first to third embodiments, the threshold value setting part 74 may set the value of the second threshold value Q2 regardless of the value of the first threshold value Q1. For example, the threshold value setting part 74 may set the first threshold value Q1 and the second threshold value Q2 individually based on the environmental information or the vehicle information, and may set the second threshold value Q2 and set the first threshold value Q1 based on the value of the second threshold value Q2. The threshold value setting part 74 may set the first threshold value Q1 and the second threshold value Q2 to different values.

As Modification 6, in the first to third embodiments, the first to third threshold values Q1 to Q3 may not be set by the threshold value setting part 74, but may be determined in advance based on an experiment, a simulation, or the like. In that case, the first to third threshold values Q1 to Q3 are stored in advance in the storage circuit 70. The same applies to the threshold values P1 and P2 and the threshold times Tr1 and r2.

As Modification 7, the configuration corresponding to the waterdrop determination part 73 may be realized by software and hardware different from those of the first to third embodiments, or a combination of the software and the hardware. In addition, the functions of the waterdrop determination part 73 and the like may be realized by the calculation processing circuits of the signal processing part 44, the ECU 15, and the like in cooperation with each other.

The invention claimed is:

1. A humidity measurement device configured to measure a humidity of a gas, the humidity measurement device comprising:
    a second-order calculation part configured to calculate a second-order differential value by performing second-order differentiation by time on a humidity signal outputted from a humidity detection part; and
    an adherence determination part configured to determine whether a liquid has adhered to the humidity detection part based on the second-order differential value obtained by the second-order calculation part.

2. The humidity measurement device according to claim 1, wherein
    the adherence determination part includes an occurrence determination part configured to determine whether the second-order differential value exceeds a predetermined occurrence threshold value, and
    the adherence determination part is configured to determine that the liquid has adhered to the humidity detection part in response to determination of the occurrence determination part that the second-order differential value exceeds the predetermined occurrence threshold value.

3. The humidity measurement device according to claim 2, wherein
    the predetermined occurrence threshold value is set to a value large enough to an extent that a maximum value of the second-order differential value of the humidity signal outputted from the humidity detection part does not reach when the humidity of the gas actually increases.

4. The humidity measurement device according to claim 2, wherein
    the adherence determination part includes an occurrence inflection determination part configured to determine whether the second-order differential value has decreased to an occurrence inflection value indicating an inflection point of a temporal change of the humidity signal after the occurrence determination part determines that the second-order differential value has increased more than the predetermined occurrence threshold value, and the adherence determination part is configured to determine that the liquid has adhered to the humidity detection part in response to determination of the occurrence inflection determination part that the second-order differential value has decreased to the occurrence inflection value.

5. The humidity measurement device according to claim 4, wherein
the adherence determination part includes an occurrence time determination part configured to determine whether the second-order differential value has decreased to the occurrence inflection value after becoming larger than the predetermined occurrence threshold value in a time shorter than a predetermined occurrence threshold time, and
the adherence determination part is configured to determine that the adherence of the liquid to the humidity detection part has occurred in response to determination of the occurrence time determination part that the second-order differential value has decreased to the occurrence inflection value in a time shorter than the predetermined occurrence threshold time.

6. The humidity measurement device according to claim 1, wherein
the adherence determination part includes a dry determination part configured to determine whether the second-order differential value has been smaller than a predetermined dry threshold value, and
the adherence determination part is configured to determine that the liquid adhered to the humidity detection part has been eliminated in response to determination of the dry determination part that the second-order differential value has been smaller than the predetermined dry threshold value.

7. The humidity measurement device according to claim 6, wherein
the predetermined dry threshold value is set to a value that is small enough to an extent that a minimum value of the second-order differential value of the humidity signal outputted from the humidity detection part does not reach when the liquid adheres to the humidity detection part.

8. The humidity measurement device according to claim 6, wherein
the adherence determination part includes a dry inflection determination part configured to determine whether the second-order differential value has increased to a dry inflection value indicating an inflection point of a temporal change in the humidity signal after the dry determination part determines that the second-order differential value has been lower than the predetermined dry threshold value, and
the adherence determination part is configured to determine that the liquid adhered to the humidity detection part has been eliminated in response to determination of the dry inflection determination part that the second-order differential value has increased to the dry inflection value.

9. The humidity measurement device according to claim 8, wherein
the adherence determination part includes a drying time determination part configured to determine whether the second-order differential value has increased to the dry inflection value after becoming smaller than the predetermined dry threshold value in a time shorter than a predetermined dry threshold time, and
the adherence determination part is configured to determine that the adherence of the liquid to the humidity detection part has occurred in response to determination of the dry time determination part that the second-order differential value has increased to the dry inflection value in a time shorter than the predetermined threshold time.

10. A control device for an internal combustion engine, the control device configured to control an operation state of the internal combustion engine supplied with an intake air, the control device comprising:
a humidity obtaining part configured to obtain a humidity of the intake air based on a humidity signal outputted from a humidity detection part according to the humidity of the intake air;
a parameter setting part configured to set an obtaining result of the humidity obtaining part as one of parameters for controlling the operation state of the internal combustion engine;
a second-order calculation part configured to calculate a second-order differential value by performing a second-order differentiation by a time on the humidity signal;
an adherence determination part configured to determine whether a liquid has adhered to the humidity detection part based on the second-order differential value obtained from the second-order calculation part; and
a substitute setting part configured to set a predetermined substitute humidity for the humidity of the intake air as one of parameters, instead of the obtaining result by the humidity detection part, in response to determination of the adherence determination part that the liquid has adhered to the humidity detection part.

11. An abnormality detection device configured to detect an adherence of a liquid to a humidity detection part, which is configured to output a humidity signal according to a humidity of a gas as an abnormality, where the abnormality is the detection of the adherence of the liquid to the humidity detection part, the abnormality detection device comprising:
a second-order calculation part configured to calculate a second-order differential value by performing a second-order differentiation by a time on the humidity signal; and
an adherence determination part configured to determine whether the liquid has adhered to the humidity detection part based on the second-order differential value obtained from the second-order calculation part.

* * * * *